US005837876A

United States Patent [19]
Conkling et al.

[11] Patent Number: 5,837,876
[45] Date of Patent: Nov. 17, 1998

[54] ROOT CORTEX SPECIFIC GENE PROMOTER

[75] Inventors: Mark A. Conkling, Fuquay-Varina; Nandini Mendu, Durham; Wen Song, Raleigh, all of N.C.

[73] Assignee: North Carolina State University, Raleigh, N.C.

[21] Appl. No.: 508,786

[22] Filed: Jul. 28, 1995

[51] Int. Cl.⁶ ........................... C12N 15/29; C12N 15/82; C12N 15/32; A01H 5/00
[52] U.S. Cl. ................... 800/205; 800/DIG. 43; 435/172.3; 435/240.4; 435/240.47; 435/252.3; 435/320.1; 435/252.2; 536/23.71; 536/24.1; 536/23.6
[58] Field of Search ................... 536/24.1, 23.6, 536/23.71; 435/240.4, 252.3, 320.1, 172.3, 252.2; 800/205, DIG. 43

[56] References Cited

U.S. PATENT DOCUMENTS

| | | | |
|---|---|---|---|
| 4,943,647 | 7/1990 | Houck et al. | 800/205 |
| 4,943,674 | 7/1990 | Houck et al. | 800/205 |
| 4,962,028 | 10/1990 | Bedbrook et al. | 435/172.3 |
| 5,097,025 | 3/1992 | Benfey et al. | 536/27 |
| 5,177,308 | 1/1993 | Barton et al. | 800/205 |
| 5,229,292 | 7/1993 | Stock et al. | 435/252.34 |
| 5,283,184 | 2/1994 | Jorgensen et al. | 435/172.3 |

FOREIGN PATENT DOCUMENTS

WO 91/13992  9/1991  WIPO ............ C12N 15/82

OTHER PUBLICATIONS

F. Fuller et al.; Soybean nodulin genes: Analysis of cDNA clones reveals several major tissue–specific sequences in nitrogen–fixing root nodules, *Proc. Natl. Acad. Sci. USA* 80:2594–2598 (1983).

L. M. Evans et al.; Distribution of root in mRNA species in other vegetative organs of pea (*Pisum sativum* L.), *Mol. Gen. Genet.* 214:153–157 (1988).

D. Bogusz et al.; Functioning haemoglobin genes in non–nodulating plants, *Letters to Nature* 331:178–180 (1988).

J.C. Sanford; The Biolistic Process, *Trends in Biotechnology* 6:299–302 (1988).

D. R. Lerner et al.; Cloning and Characterization of Root–Specific Barley Lectin, *Plant Physiol,* 91:124–129 (1989).

Y. T. Yamamoto; A tobacco root–specific gene; characterization and regulation of its transcription, Ph.D. Thesis submitted to the Graduate Faculty of North Carolina State University, Genetics Dept. (1989).

Y. T. Yamamoto; A tobacco root–specific gene; characterization and regulation of its expression, *J. Cell Biochem.* 13(D) (Suppl) (1989).

M. A. Conkling et al.; Isolation of Transcriptionally Regulated Root–Specific Genes from Tobacco, *Plant Physiol.* 93:1203–1211 (1989).

Y. T. Yamamoto et al.; Root–specific genes from tobacco and *Arabidopsis homologous* to an evolutionary conserved gene family of membrane channel proteins, *Nucleic Acids Research* 18:7449 (1990).

Y. T. Yamamoto et al.; Characterization of cis–Acting Sequences Regulating Root–Specific Gene Expression in Tobacco, *The Plant Cell* 3:371–382 (1991).

F.C. Hsu et al., Phloem Mobility of Xenobiotics VI. a phloem–mobile pro–nematocide based on oxamyl exhibiting root–specific activation in transgenic tobacco, *Pestic. Sci.* 44, 9–19 (1995).

B. Keller et al.; Specific expression of novel cell wall hydroxyproline–rich glycoprotein gene in lateral root initiation, *Genes & Dev.,* 3:1639–1646 (1989).

Conkling et al. Plant Physiol. vol. 93 pp. 1203–1211 (1990) Isolation of Transcriptionally Regulated . . . .

*Primary Examiner*—David T. Fox
*Assistant Examiner*—Thomas Haas
*Attorney, Agent, or Firm*—Bell, Seltzer, Park & Gibson

[57] ABSTRACT

An isolated DNA molecule which comprises a DNA promoter sequence which directs root cortex specific transcription of a downstream heterologous DNA segment in a plant cell. A DNA construct which comprises an expression cassette comprising, in the 5' to 3' direction, a promoter of the present invention and a heterologous DNA segment positioned downstream from the promoter and operatively associated therewith. Transformed plants, such as tobacco plants, comprise transformed plant cells containing a heterologous DNA construct comprising an expression cassette as described above.

22 Claims, 5 Drawing Sheets

```
CTCGAGGATC TAAATTGTGA GTTCAATCTC TTCCCTATTG GATTGATTAT CCTTTCTTTT    60
CTTCCAATTT GTGTTTCTTT TTGCCTAATT TATTGTGTTA TCCCCTTTAT CCTATTTTGT   120
TTCTTTACTT ATTTATTTGC TTCTATGTCT TTGTACAAAG ATTTAAACTC TATGGCACAT   180
ATTTTAAAGT TGTTAGAAAA TAAATTCTTT CAAGATTGAT GAAAGAACTT TTTAATTGTA   240
GATATTTCGT AGATTTTATT CTCTTACTAC CAATATAACG CTTGAATTGA CGAAAATTTG   300
TGTCCAAATA TCTAGCAAAA AGGTATCCAA TGAAAATATA TCATATGTGA TCTTCAAATC   360
TTGTGTCTTA TGCAAGATTG ATACTTTGTT CAATGGAAGA GATTGTGTGC ATATTTTTAA   420
AATTTTTATT AGTAATAAAG ATTCTATATA GCTGTTATAG AGGGATAATT TTACAAAGAA   480
CACTATAAAT ATGATTGTTG TTGTTAGGGT GTCAATGGTT CGGTTCGACT GGTTATTTTA   540
TAAAATTTGT ACCATACCAT TTTTTTCGAT ATTCTATTTT GTATAACCAA AATTAGACTT   600
TTCGAAATCG TCCCAATCAT GTCGGTTTCA CTTCGGTATC GGTACCGTTC GGTTAATTTT   660
CATTTTTTTT TAAATGTCAT TAAAATTCAC TAGTAAAAAT AGAATGCAAT AACATACGTT   720
CTTTTATAGG ACTTAGCAAA AGCTCTCTAG ACATTTTTAC TGTTTAAAGG ATAATGAATT   780
AAAAAAACATG AAAGATGGCT AGAGTATAGA TACACAACTA TTCGACAGCA ACGTAAAAGA   840
AACCAAGTAA AAGCAAAGAA AATATAAATC ACACGAGTGG AAAGATATTA ACCAAGTTGG   900
GATTCAAGAA TAAAGTCTAT ATTAAATATT CAAAAGATA AATTTAAATA ATATGAAAGG   960
AAACATATTC AATACATTGT AGTTTGCTAC TCATAATCGC TAGAATACTT TGTGCCTTGC  1020
TAATAAAGAT ACTTGAAATA GCTTAGTTTA AATATAAATA GCATAATAGA TTTTAGGAAT  1080
TAGTATTTTG AGTTTAATTA CTTATTGACT TGTAACAGTT TTTATAATTC CAAGGCCCAT  1140
GAAAAATTTA ATGCTTTATT AGTTTTAAAC TTACTATATA AATTTTTCAT ATGTAAAATT  1200
TAATCGGTAT AGTTCGATAT TTTTTCAATT TATTTTTATA AAATAAAAAA CTTACCCTAA  1260
TTATCGGTAC AGTTATAGAT TTATATAAAA ATCTACGGTT CTTCAGAAGA AACCTAAAAA  1320
TCGGTTCGGT GCGGACGGTT CGATCGGTTT AGTCGATTTT CAAATATTCA TTGACACTCC  1380
TAGTTGTTGT TATAGGTAAA AAGCAGTTAC AGAGAGGTAA AATATAACTT AAAAAATCAG  1440
TTCTAAGGAA AAATTGACTT TTATAGTAAA TGACTGTTAT ATAAGGATGT TGTTACAGAG  1500
AGGTATGAGT GTAGTTGGTA AATTATGTTC TTGACGGTGT ATGTCACATA TTATTTATTA  1560
AAACTAGAAA AAACAGCGTC AAAACTAGCA AAAATCCAAC GGACAAAAAA ATCGGCTGAA  1620
TTTGATTTGG TTCCAACATT TAAAAAAGTT TCAGTGAGAA AGAATCGGTG ACTGTTGATG  1680
ATATAAACAA AGGGCACATT GGTCAATAAC CATAAAAAAT TATATGACAG CTACAGTTGG  1740
TAGCATGTGC TCAGCTATTG AACAAATCTA AAGAAGGTAC ATCTGTAACC GGAACACCAC  1800
TTAAATGACT AAATTACCCT CATCAGAAAG CAGATGGAGT GCTACAAATA ACACACTATT  1860
CAACAACCAT AAATAAAACG TGTTCAGCTA CTAAAACAAA TATAAATAAA TCTATGTTTG  1920
TAAGCACTCC AGCCATGTTA ATGGAGTGCT ATTGCCTGTT AACTCTCACT TATAAAATAG  1980
TAGTAGAAAA AATATGAACC AAAACACAAC                                   2010
```

FIG. 2.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 2010 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| CTCGAGGATC | TAAATTGTGA | GTTCAATCTC | TTCCCTATTG | GATTGATTAT | CCTTTCTTTT | 60 |
| CTTCCAATTT | GTGTTTCTTT | TTGCCTAATT | TATTGTGTTA | TCCCCTTTAT | CCTATTTTGT | 120 |
| TTCTTTACTT | ATTTATTTGC | TTCTATGTCT | TTGTACAAAG | ATTTAAACTC | TATGGCACAT | 180 |
| ATTTTAAAGT | TGTTAGAAAA | TAAATTCTTT | CAAGATTGAT | GAAAGAACTT | TTTAATTGTA | 240 |
| GATATTTCGT | AGATTTTATT | CTCTTACTAC | CAATATAACG | CTTGAATTGA | CGAAAATTTG | 300 |
| TGTCCAAATA | TCTAGCAAAA | AGGTATCCAA | TGAAAATATA | TCATATGTGA | TCTTCAAATC | 360 |
| TTGTGTCTTA | TGCAAGATTG | ATACTTTGTT | CAATGGAAGA | GATTGTGTGC | ATATTTTAA | 420 |
| AATTTTTATT | AGTAATAAAG | ATTCTATATA | GCTGTTATAG | AGGGATAATT | TTACAAAGAA | 480 |
| CACTATAAAT | ATGATTGTTG | TTGTTAGGGT | GTCAATGGTT | CGGTTCGACT | GGTTATTTTA | 540 |
| TAAAATTTGT | ACCATACCAT | TTTTTCGAT | ATTCTATTTT | GTATAACCAA | AATTAGACTT | 600 |
| TTCGAAATCG | TCCCAATCAT | GTCGGTTTCA | CTTCGGTATC | GGTACCGTTC | GGTTAATTTT | 660 |
| CATTTTTTTT | TAAATGTCAT | TAAAATTCAC | TAGTAAAAAT | AGAATGCAAT | AACATACGTT | 720 |
| CTTTTATAGG | ACTTAGCAAA | AGCTCTCTAG | ACATTTTTAC | TGTTTAAAGG | ATAATGAATT | 780 |
| AAAAAACATG | AAAGATGGCT | AGAGTATAGA | TACACAACTA | TTCGACAGCA | ACGTAAAAGA | 840 |
| AACCAAGTAA | AAGCAAAGAA | AATATAAATC | ACACGAGTGG | AAAGATATTA | ACCAAGTTGG | 900 |
| GATTCAAGAA | TAAAGTCTAT | ATTAAATATT | CAAAAGATA | AATTTAAATA | ATATGAAAGG | 960 |
| AAACATATTC | AATACATTGT | AGTTTGCTAC | TCATAATCGC | TAGAATACTT | TGTGCCTTGC | 1020 |
| TAATAAAGAT | ACTTGAAATA | GCTTAGTTTA | AATATAAATA | GCATAATAGA | TTTTAGGAAT | 1080 |
| TAGTATTTTG | AGTTTAATTA | CTTATTGACT | TGTAACAGTT | TTTATAATTC | CAAGGCCCAT | 1140 |
| GAAAATTTA | ATGCTTTATT | AGTTTTAAAC | TTACTATATA | AATTTTTCAT | ATGTAAAATT | 1200 |
| TAATCGGTAT | AGTTCGATAT | TTTTTCAATT | TATTTTTATA | AAATAAAAAA | CTTACCCTAA | 1260 |
| TTATCGGTAC | AGTTATAGAT | TTATATAAAA | ATCTACGGTT | CTTCAGAAGA | AACCTAAAAA | 1320 |
| TCGGTTCGGT | GCGGACGGTT | CGATCGGTTT | AGTCGATTTT | CAAATATTCA | TTGACACTCC | 1380 |
| TAGTTGTTGT | TATAGGTAAA | AAGCAGTTAC | AGAGAGGTAA | AATATAACTT | AAAAAATCAG | 1440 |
| TTCTAAGGAA | AAATTGACTT | TTATAGTAAA | TGACTGTTAT | ATAAGGATGT | TGTTACAGAG | 1500 |
| AGGTATGAGT | GTAGTTGGTA | AATTATGTTC | TTGACGGTGT | ATGTCACATA | TTATTTATTA | 1560 |
| AAACTAGAAA | AAACAGCGTC | AAAACTAGCA | AAAATCCAAC | GGACAAAAA | ATCGGCTGAA | 1620 |
| TTTGATTTGG | TTCCAACATT | TAAAAAGTT | TCAGTGAGAA | AGAATCGGTG | ACTGTTGATG | 1680 |
| ATATAAACAA | AGGGCACATT | GGTCAATAAC | CATAAAAAAT | TATATGACAG | CTACAGTTGG | 1740 |
| TAGCATGTGC | TCAGCTATTG | AACAAATCTA | AAGAAGGTAC | ATCTGTAACC | GGAACACCAC | 1800 |

| | | | | | |
|---|---|---|---|---|---|
| TTAAATGACT | AAATTACCCT | CATCAGAAAG | CAGATGGAGT | GCTACAAATA | ACACACTATT | 1860
| CAACAACCAT | AAATAAAACG | TGTTCAGCTA | CTAAAACAAA | TATAAATAAA | TCTATGTTTG | 1920
| TAAGCACTCC | AGCCATGTTA | ATGGAGTGCT | ATTGCCTGTT | AACTCTCACT | TATAAAATAG | 1980
| TAGTAGAAAA | AATATGAACC | AAAACACAAC | | | | 2010

( 2 ) INFORMATION FOR SEQ ID NO:2:

( i ) SEQUENCE CHARACTERISTICS:
        ( A ) LENGTH: 1988 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| CTCGAGGATC | TAAATTGTGA | GTTCAATCTC | TTCCCTATTG | GATTGATTAT | CCTTTCTTTT | 60
| CTTCCAATTT | GTGTTTCTTT | TTGCCTAATT | TATTGTGTTA | TCCCCTTTAT | CCTATTTTGT | 120
| TTCTTTACTT | ATTTATTTGC | TTCTATGTCT | TTGTACAAAG | ATTTAAACTC | TATGGCACAT | 180
| ATTTTAAAGT | TGTTAGAAAA | TAAATTCTTT | CAAGATTGAT | GAAAGAACTT | TTTAATTGTA | 240
| GATATTTCGT | AGATTTTATT | CTCTTACTAC | CAATATAACG | CTTGAATTGA | CGAAAATTTG | 300
| TGTCCAAATA | TCTAGCAAAA | AGGTATCCAA | TGAAAATATA | TCATATGTGA | TCTTCAAATC | 360
| TTGTGTCTTA | TGCAAGATTG | ATACTTTGTT | CAATGGAAGA | GATTGTGTGC | ATATTTTAA | 420
| AATTTTTATT | AGTAATAAAG | ATTCTATATA | GCTGTTATAG | AGGGATAATT | TTACAAAGAA | 480
| CACTATAAAT | ATGATTGTTG | TTGTTAGGGT | GTCAATGGTT | CGGTTCGACT | GGTTATTTTA | 540
| TAAAATTTGT | ACCATACCAT | TTTTTTCGAT | ATTCTATTTT | GTATAACCAA | AATTAGACTT | 600
| TTCGAAATCG | TCCCAATCAT | GTCGGTTTCA | CTTCGGTATC | GGTACCGTTC | GGTTAATTTT | 660
| CATTTTTTTT | TAAATGTCAT | TAAAATTCAC | TAGTAAAAAT | AGAATGCAAT | AACATACGTT | 720
| CTTTTATAGG | ACTTAGCAAA | AGCTCTCTAG | ACATTTTTAC | TGTTTAAAGG | ATAATGAATT | 780
| AAAAACATG | AAAGATGGCT | AGAGTATAGA | TACACAACTA | TTCGACAGCA | ACGTAAAAGA | 840
| AACCAAGTAA | AAGCAAAGAA | AATATAAATC | ACACGAGTGG | AAAGATATTA | ACCAAGTTGG | 900
| GATTCAAGAA | TAAAGTCTAT | ATTAAATATT | CAAAAGATA | AATTTAAATA | ATATGAAAGG | 960
| AAACATATTC | AATACATTGT | AGTTTGCTAC | TCATAATCGC | TAGAATACTT | TGTGCCTTGC | 1020
| TAATAAAGAT | ACTTGAAATA | GCTTAGTTTA | AATATAAATA | GCATAATAGA | TTTTAGGAAT | 1080
| TAGTATTTTG | AGTTTAATTA | CTTATTGACT | TGTAACAGTT | TTTATAATTC | CAAGGCCCAT | 1140
| GAAAATTTA | ATGCTTTATT | AGTTTTAAAC | TTACTATATA | AATTTTTCAT | ATGTAAAATT | 1200
| TAATCGGTAT | AGTTCGATAT | TTTTTCAATT | TATTTTTATA | AAATAAAAAA | CTTACCCTAA | 1260
| TTATCGGTAC | AGTTATAGAT | TTATATAAAA | ATCTACGGTT | CTTCAGAAGA | AACCTAAAAA | 1320
| TCGGTTCGGT | GCGGACGGTT | CGATCGGTTT | AGTCGATTTT | CAAATATTCA | TTGACACTCC | 1380
| TAGTTGTTGT | TATAGGTAAA | AAGCAGTTAC | AGAGAGGTAA | AATATAACTT | AAAAAATCAG | 1440
| TTCTAAGGAA | AAATTGACTT | TTATAGTAAA | TGACTGTTAT | ATAAGGATGT | TGTTACAGAG | 1500
| AGGTATGAGT | GTAGTTGGTA | AATTATGTTC | TTGACGGTGT | ATGTCACATA | TTATTTATTA | 1560
| AAACTAGAAA | AAACAGCGTC | AAAACTAGCA | AAAATCCAAC | GGACAAAAAA | ATCGGCTGAA | 1620
| TTTGATTTGG | TTCCAACATT | TAAAAAGTT | TCAGTGAGAA | AGAATCGGTG | ACTGTTGATG | 1680
| ATATAAACAA | AGGGCACATT | GGTCAATAAC | CATAAAAAAT | TATATGACAG | CTACAGTTGG | 1740
| TAGCATGTGC | TCAGCTATTG | AACAAATCTA | AAGAAGGTAC | ATCTGTAACC | GGAACACCAC | 1800

| | | | | | |
|---|---|---|---|---|---|
| TTAAATGACT | AAATTACCCT | CATCAGAAAG | CAGATGGAGT | GCTACAAATA | ACACACTATT | 1860 |
| CAACAACCAT | AAATAAAACG | TGTTCAGCTA | CTAAAACAAA | TATAAATAAA | TCTATGTTTG | 1920 |
| TAAGCACTCC | AGCCATGTTA | ATGGAGTGCT | ATTGCCTGTT | AACTCTCACT | TATAAAATAG | 1980 |
| TAGTAGAA | | | | | | 1988 |

( 2 ) INFORMATION FOR SEQ ID NO:3:

( i ) SEQUENCE CHARACTERISTICS:
    ( A ) LENGTH: 1372 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| TCATGTCGGT | TTCACTTCGG | TATCGGTACC | GTTCGGTTAA | TTTTCATTTT | TTTTAAATG | 60 |
| TCATTAAAAT | TCACTAGTAA | AAATAGAATG | CAATAACATA | CGTTCTTTTA | TAGGACTTAG | 120 |
| CAAAGCTCT | CTAGACATTT | TTACTGTTTA | AAGGATAATG | AATTAAAAAA | CATGAAAGAT | 180 |
| GGCTAGAGTA | TAGATACACA | ACTATTCGAC | AGCAACGTAA | AAGAAACCAA | GTAAAAGCAA | 240 |
| AGAAAATATA | AATCACACGA | GTGGAAAGAT | ATTAACCAAG | TTGGGATTCA | AGAATAAAGT | 300 |
| CTATATTAAA | TATTCAAAAA | GATAAATTTA | AATAATATGA | AAGGAAACAT | ATTCAATACA | 360 |
| TTGTAGTTTG | CTACTCATAA | TCGCTAGAAT | ACTTTGTGCC | TTGCTAATAA | AGATACTTGA | 420 |
| AATAGCTTAG | TTTAAATATA | AATAGCATAA | TAGATTTTAG | GAATTAGTAT | TTTGAGTTTA | 480 |
| ATTACTTATT | GACTTGTAAC | AGTTTTTATA | ATTCCAAGGC | CCATGAAAAA | TTTAATGCTT | 540 |
| TATTAGTTTT | AAACTTACTA | TATAAATTTT | TCATATGTAA | AATTTAATCG | GTATAGTTCG | 600 |
| ATATTTTTC | AATTTATTTT | TATAAAATAA | AAAACTTACC | CTAATTATCG | GTACAGTTAT | 660 |
| AGATTTATAT | AAAAATCTAC | GGTTCTTCAG | AAGAAACCTA | AAAATCGGTT | CGGTGCGGAC | 720 |
| GGTTCGATCG | GTTTAGTCGA | TTTTCAAATA | TTCATTGACA | CTCCTAGTTG | TTGTTATAGG | 780 |
| TAAAAGCAG | TTACAGAGAG | GTAAAATATA | ACTTAAAAAA | TCAGTTCTAA | GGAAAAATTG | 840 |
| ACTTTTATAG | TAAATGACTG | TTATATAAGG | ATGTTGTTAC | AGAGAGGTAT | GAGTGTAGTT | 900 |
| GGTAAATTAT | GTTCTTGACG | GTGTATGTCA | CATATTATTT | ATTAAAACTA | GAAAAAACAG | 960 |
| CGTCAAAACT | AGCAAAAATC | CAACGGACAA | AAAAATCGGC | TGAATTTGAT | TTGGTTCCAA | 1020 |
| CATTTAAAAA | AGTTTCAGTG | AGAAAGAATC | GGTGACTGTT | GATGATATAA | ACAAAGGGCA | 1080 |
| CATTGGTCAA | TAACCATAAA | AAATTATATG | ACAGCTACAG | TTGGTAGCAT | GTGCTCAGCT | 1140 |
| ATTGAACAAA | TCTAAAGAAG | GTACATCTGT | AACCGGAACA | CCACTTAAAT | GACTAAATTA | 1200 |
| CCCTCATCAG | AAAGCAGATG | GAGTGCTACA | AATAACACAC | TATTCAACAA | CCATAAATAA | 1260 |
| AACGTGTTCA | GCTACTAAAA | CAAATATAAA | TAAATCTATG | TTTGTAAGCA | CTCCAGCCAT | 1320 |
| GTTAATGGAG | TGCTATTGCC | TGTTAACTCT | CACTTATAAA | ATAGTAGTAG | AA | 1372 |

( 2 ) INFORMATION FOR SEQ ID NO:4:

( i ) SEQUENCE CHARACTERISTICS:
    ( A ) LENGTH: 1294 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

| | | | | | | |
|---|---|---|---|---|---|---|
| AAAAATAGAA | TGCAATAACA | TACGTTCTTT | TATAGGACTT | AGCAAAAGCT | CTCTAGACAT | 60 |
| TTTTACTGTT | TAAAGGATAA | TGAATTAAAA | AACATGAAAG | ATGGCTAGAG | TATAGATACA | 120 |
| CAACTATTCG | ACAGCAACGT | AAAAGAAACC | AAGTAAAAGC | AAAGAAAATA | TAAATCACAC | 180 |
| GAGTGGAAAG | ATATTAACCA | AGTTGGGATT | CAAGAATAAA | GTCTATATTA | AATATTCAAA | 240 |
| AAGATAAATT | TAAATAATAT | GAAGGAAAC | ATATTCAATA | CATTGTAGTT | TGCTACTCAT | 300 |
| AATCGCTAGA | ATACTTTGTG | CCTTGCTAAT | AAAGATACTT | GAAATAGCTT | AGTTTAAATA | 360 |
| TAAATAGCAT | AATAGATTTT | AGGAATTAGT | ATTTTGAGTT | TAATTACTTA | TTGACTTGTA | 420 |
| ACAGTTTTTA | TAATTCCAAG | GCCCATGAAA | AATTTAATGC | TTTATTAGTT | TTAAACTTAC | 480 |
| TATATAAATT | TTTCATATGT | AAAATTTAAT | CGGTATAGTT | CGATATTTTT | TCAATTTATT | 540 |
| TTTATAAAAT | AAAAAACTTA | CCCTAATTAT | CGGTACAGTT | ATAGATTTAT | ATAAAAATCT | 600 |
| ACGGTTCTTC | AGAAGAAACC | TAAAAATCGG | TTCGGTGCGG | ACGGTTCGAT | CGGTTTAGTC | 660 |
| GATTTTCAAA | TATTCATTGA | CACTCCTAGT | TGTTGTTATA | GGTAAAAAGC | AGTTACAGAG | 720 |
| AGGTAAAATA | TAACTTAAAA | AATCAGTTCT | AAGGAAAAAT | TGACTTTTAT | AGTAAATGAC | 780 |
| TGTTATATAA | GGATGTTGTT | ACAGAGAGGT | ATGAGTGTAG | TTGGTAAATT | ATGTTCTTGA | 840 |
| CGGTGTATGT | CACATATTAT | TTATTAAAAC | TAGAAAAAAC | AGCGTCAAAA | CTAGCAAAAA | 900 |
| TCCAACGGAC | AAAAAAATCG | GCTGAATTTG | ATTTGGTTCC | AACATTTAAA | AAAGTTTCAG | 960 |
| TGAGAAAGAA | TCGGTGACTG | TTGATGATAT | AAACAAAGGG | CACATTGGTC | AATAACCATA | 1020 |
| AAAAATTATA | TGACAGCTAC | AGTTGGTAGC | ATGTGCTCAG | CTATTGAACA | AATCTAAAGA | 1080 |
| AGGTACATCT | GTAACCGGAA | CACCACTTAA | ATGACTAAAT | TACCCTCATC | AGAAAGCAGA | 1140 |
| TGGAGTGCTA | CAAATAACAC | ACTATTCAAC | AACCATAAAT | AAAACGTGTT | CAGCTACTAA | 1200 |
| AACAAATATA | AATAAATCTA | TGTTTGTAAG | CACTCCAGCC | ATGTTAATGG | AGTGCTATTG | 1260 |
| CCTGTTAACT | CTCACTTATA | AAATAGTAGT | AGAA | | | 1294 |

( 2 ) INFORMATION FOR SEQ ID NO:5:

( i ) SEQUENCE CHARACTERISTICS:
        ( A ) LENGTH: 1030 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | | |
|---|---|---|---|---|---|---|
| GGAAACATAT | TCAATACATT | GTAGTTTGCT | ACTCATAATC | GCTAGAATAC | TTTGTGCCTT | 60 |
| GCTAATAAAG | ATACTTGAAA | TAGCTTAGTT | TAAATATAAA | TAGCATAATA | GATTTTAGGA | 120 |
| ATTAGTATTT | TGAGTTTAAT | TACTTATTGA | CTTGTAACAG | TTTTTATAAT | TCCAAGGCCC | 180 |
| ATGAAAAATT | TAATGCTTTA | TTAGTTTTAA | ACTTACTATA | TAAATTTTTC | ATATGTAAAA | 240 |
| TTTAATCGGT | ATAGTTCGAT | ATTTTTTCAA | TTTATTTTTA | TAAATAAAA | AACTTACCCT | 300 |
| AATTATCGGT | ACAGTTATAG | ATTTATATAA | AAATCTACGG | TTCTTCAGAA | GAAACCTAAA | 360 |
| AATCGGTTCG | GTGCGGACGG | TTCGATCGGT | TTAGTCGATT | TTCAAATATT | CATTGACACT | 420 |
| CCTAGTTGTT | GTTATAGGTA | AAAGCAGTT | ACAGAGAGGT | AAAATATAAC | TTAAAAAATC | 480 |
| AGTTCTAAGG | AAAAATTGAC | TTTTATAGTA | AATGACTGTT | ATATAAGGAT | GTTGTTACAG | 540 |
| AGAGGTATGA | GTGTAGTTGG | TAAATTATGT | TCTTGACGGT | GTATGTCACA | TATTATTTAT | 600 |
| TAAAACTAGA | AAAAACAGCG | TCAAAACTAG | CAAAAATCCA | ACGGACAAAA | AATCGGCTG | 660 |

| | | | | | |
|---|---|---|---|---|---|
| AATTTGATTT | GGTTCCAACA | TTTAAAAAAG | TTTCAGTGAG | AAAGAATCGG | TGACTGTTGA | 720
| TGATATAAAC | AAAGGGCACA | TTGGTCAATA | ACCATAAAAA | ATTATATGAC | AGCTACAGTT | 780
| GGTAGCATGT | GCTCAGCTAT | TGAACAAATC | TAAAGAAGGT | ACATCTGTAA | CCGGAACACC | 840
| ACTTAAATGA | CTAAATTACC | CTCATCAGAA | AGCAGATGGA | GTGCTACAAA | TAACACACTA | 900
| TTCAACAACC | ATAAATAAAA | CGTGTTCAGC | TACTAAAACA | AATATAAATA | AATCTATGTT | 960
| TGTAAGCACT | CCAGCCATGT | TAATGGAGTG | CTATTGCCTG | TTAACTCTCA | CTTATAAAAT | 1020
| AGTAGTAGAA | | | | | | 1030

( 2 ) INFORMATION FOR SEQ ID NO:6:

( i ) SEQUENCE CHARACTERISTICS:
        ( A ) LENGTH: 722 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
| GTACAGTTAT | AGATTTATAT | AAAAATCTAC | GGTTCTTCAG | AAGAAACCTA | AAAATCGGTT | 60
| CGGTGCGGAC | GGTTCGATCG | GTTAGTCGA | TTTTCAAATA | TTCATTGACA | CTCCTAGTTG | 120
| TTGTTATAGG | TAAAAAGCAG | TTACAGAGAG | GTAAAATATA | ACTTAAAAAA | TCAGTTCTAA | 180
| GGAAAAATTG | ACTTTTATAG | TAAATGACTG | TTATATAAGG | ATGTTGTTAC | AGAGAGGTAT | 240
| GAGTGTAGTT | GGTAAATTAT | GTTCTTGACG | GTGTATGTCA | CATATTATTT | ATTAAAACTA | 300
| GAAAAAACAG | CGTCAAAACT | AGCAAAAATC | CAACGGACAA | AAAAATCGGC | TGAATTTGAT | 360
| TTGGTTCCAA | CATTTAAAAA | AGTTTCAGTG | AGAAAGAATC | GGTGACTGTT | GATGATATAA | 420
| ACAAAGGGCA | CATTGGTCAA | TAACCATAAA | AAATTATATG | ACAGCTACAG | TTGGTAGCAT | 480
| GTGCTCAGCT | ATTGAACAAA | TCTAAAGAAG | GTACATCTGT | AACCGGAACA | CCACTTAAAT | 540
| GACTAAATTA | CCCTCATCAG | AAAGCAGATG | GAGTGCTACA | AATAACACAC | TATTCAACAA | 600
| CCATAAATAA | AACGTGTTCA | GCTACTAAAA | CAAATATAAA | TAAATCTATG | TTTGTAAGCA | 660
| CTCCAGCCAT | GTTAATGGAG | TGCTATTGCC | TGTTAACTCT | CACTTATAAA | ATAGTAGTAG | 720
| AA | | | | | | 722

( 2 ) INFORMATION FOR SEQ ID NO:7:

( i ) SEQUENCE CHARACTERISTICS:
        ( A ) LENGTH: 574 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---|
| AGGTAAAATA | TAACTTAAAA | AATCAGTTCT | AAGGAAAAAT | TGACTTTTAT | AGTAAATGAC | 60
| TGTTATATAA | GGATGTTGTT | ACAGAGAGGT | ATGAGTGTAG | TTGGTAAATT | ATGTTCTTGA | 120
| CGGTGTATGT | CACATATTAT | TTATTAAAAC | TAGAAAAAAC | AGCGTCAAAA | CTAGCAAAAA | 180
| TCCAACGGAC | AAAAAAATCG | GCTGAATTTG | ATTTGGTTCC | AACATTTAAA | AAAGTTTCAG | 240
| TGAGAAAGAA | TCGGTGACTG | TTGATGATAT | AAACAAAGGG | CACATTGGTC | AATAACCATA | 300
| AAAAATTATA | TGACAGCTAC | AGTTGGTAGC | ATGTGCTCAG | CTATTGAACA | AATCTAAAGA | 360
| AGGTACATCT | GTAACCGGAA | CACCACTTAA | ATGACTAAAT | TACCCTCATC | AGAAAGCAGA | 420

-continued

| | | | | | | |
|---|---|---|---|---|---|---|
|TGGAGTGCTA|CAAATAACAC|ACTATTCAAC|AACCATAAAT|AAAACGTGTT|CAGCTACTAA|480|
|AACAAATATA|AATAAATCTA|TGTTTGTAAG|CACTCCAGCC|ATGTTAATGG|AGTGCTATTG|540|
|CCTGTTAACT|CTCACTTATA|AAATAGTAGT|AGAA|||574|

( 2 ) INFORMATION FOR SEQ ID NO:8:

( i ) SEQUENCE CHARACTERISTICS:
        ( A ) LENGTH: 523 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | | |
|---|---|---|---|---|---|---|
|GTAAATGACT|GTTATATAAG|GATGTTGTTA|CAGAGAGGTA|TGAGTGTAGT|TGGTAAATTA|60|
|TGTTCTTGAC|GGTGTATGTC|ACATATTATT|TATTAAAACT|AGAAAAAACA|GCGTCAAAAC|120|
|TAGCAAAAAT|CCAACGGACA|AAAAAATCGG|CTGAATTTGA|TTTGGTTCCA|ACATTTAAAA|180|
|AAGTTTCAGT|GAGAAAGAAT|CGGTGACTGT|TGATGATATA|AACAAAGGGC|ACATTGGTCA|240|
|ATAACCATAA|AAAATTATAT|GACAGCTACA|GTTGGTAGCA|TGTGCTCAGC|TATTGAACAA|300|
|ATCTAAAGAA|GGTACATCTG|TAACCGGAAC|ACCACTTAAA|TGACTAAATT|ACCCTCATCA|360|
|GAAAGCAGAT|GGAGTGCTAC|AAATAACACA|CTATTCAACA|ACCATAAATA|AAACGTGTTC|420|
|AGCTACTAAA|ACAAATATAA|ATAAATCTAT|GTTTGTAAGC|ACTCCAGCCA|TGTTAATGGA|480|
|GTGCTATTGC|CTGTTAACTC|TCACTTATAA|AATAGTAGTA|GAA||523|

( 2 ) INFORMATION FOR SEQ ID NO:9:

( i ) SEQUENCE CHARACTERISTICS:
        ( A ) LENGTH: 220 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| | | | | | | |
|---|---|---|---|---|---|---|
|TAAAGAAGGT|ACATCTGTAA|CCGGAACACC|ACTTAAATGA|CTAAATTACC|CTCATCAGAA|60|
|AGCAGATGGA|GTGCTACAAA|TAACACACTA|TTCAACAACC|ATAAATAAAA|CGTGTTCAGC|120|
|TACTAAAACA|AATATAAATA|AATCTATGTT|TGTAAGCACT|CCAGCCATGT|TAATGGAGTG|180|
|CTATTGCCTG|TTAACTCTCA|CTTATAAAAT|AGTAGTAGAA|||220|

ROOT CORTEX SPECIFIC GENE PROMOTER

This invention was made with government support under Grant No. MCB-9206506 from the National Science Foundation. The government may have certain rights to this invention.

FIELD OF THE INVENTION

This invention relates to tissue-specific gene promoters, and particularly relates to a promoter which is active in the root cortex of plants.

BACKGROUND OF THE INVENTION

A promoter is a DNA sequence which flanks a transcribed gene, and to which RNA polymerase must bind if it is to transcribe the flanking gene into messenger RNA. A promoter may consist of a number of different regulatory elements which affect a structural gene operationally associated with the promoter in different ways. For example, a regulatory gene may enhance or repress expression of an associated structural gene, subject that gene to developmental regulation, or contribute to the tissue-specific regulation of that gene. Modifications to promoters can make possible optional patterns of gene expression, using recombinant DNA procedures. See, e.g., Old and Primrose, *Principles of Gene Manipulation* (4th Ed., 1989).

One example of a plant promoter is the promoter found flanking the gene for the small subunit ribulose-1,5-bisphosphate carboxylase in Petunia. See U.S. Pat. No. 4,962,028. Another example is the promoter which comprises the 5' flanking region of the wheat Em gene. See EPO Appln. No. 335528. Still another example is the stress-inducible regulatory element disclosed in EPO Appln. No. 0 330 479.

Despite their important role in plant development, relatively little work has been done on the regulation of gene expression in roots. In part the deficiency results from a paucity of readily identifiable, root-specific biochemical functions whose genes may be easily cloned and studied. Evans et al., *Mol. Gen. Genet.* 214, 153–157 (1988), tried unsuccessfully to isolate root-specific cDNA clones from pea, concluding that root-specific mRNA species (if present) are only present at a very low level of abundance in the root mRNA population. Fuller et al., *Proc. Natl. Acad. Sci. USA* 80, 2594–2598 (1983), have cloned and characterized a number of root nodule-specific genes. Comparisons of the DNA sequences 5' of the initiation of transcription reveal a repeated octanucleotide present in the three genes examined. Unfortunately, the lack of efficient transformation/regeneration systems for most Leguminaceae has hampered the functional analysis of such cis-acting sequences. Bogusz et al., *Nature* 331, 178–180 (1988), isolated a haemoglobin gene expressed specifically in roots of non-nodulating plants by its homology with the haemoglobin gene of closely related, nodulating species. Keller and Lamb, *Genes & Dev.* 3, 1639–1646 (1989), isolated a gene encoding a cell wall hydroxyproline rich glycoprotein expressed during lateral root initiation. Lerner and Raikhel, *Plant Physiol.* 91, 124–129 (1989), recently reported the cloning and characterization of a barley root-specific lectin.

Many plant pathogens and pests damage plant roots, causing serious crop damage and loss. The root tissue most often damaged is the root cortex, a layer composed primarily of storage parenchyma which underlies the epidermis layer and surrounds the central vascular cylinder of the root. The root cortex may additionally contain schlerenchyma, secretory cells, resin ducts and other structures and cells types. The cells of the root cortex exhibit morphological and developmental similarities with cortical cells of the aerial shoot.

To impart useful traits to plants by the expression of foreign genes using genetic engineering techniques, a variety of tissue-specific promoters will be required to allow new traits to be expressed selectively in the appropriate plant tissues. The present invention is based upon our continuing investigations in connection with this problem.

SUMMARY OF THE INVENTION

The present invention is based on the identification of the tobacco RD2 (TobRD2) promoter, which directs root cortex specific expression of associated genes. A first aspect of the present invention is an isolated DNA molecule which directs root cortex specific transcription of a downstream heterologous DNA segment in a plant cell, the isolated DNA molecule having a sequence selected from the group consisting of (a) SEQ ID NOs:1–9 provided herein, and (b) DNA sequences which hybridize to any of SEQ ID NOS:1–9 under stringent conditions, and which direct root cortex specific transcription of a downstream heterologous DNA segment in a plant cell.

A further aspect of the present invention is an expression cassette comprising a Tobacco RD2 promoter and a heterologous DNA segment positioned downstream from, and operatively associated with, the promoter.

A further aspect of the present invention is an expression cassette comprising a root cortex specific promoter and a heterologous DNA segment, the sequence of the root cortex specific promoter selected from SEQ ID NOS:1–9 provided herein, and DNA sequences which hybridize to any of SEQ ID NOS:1–9 under stringent conditions, and which directs root cortex specific transcription.

Further aspects of the present invention are plant cells containing the above described expression cassettes, methods of making transformed plants from such plant cells, and the transformed plants comprising such transformed plant cells.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 2 is a 2010 base pair sequence (SEQ ID NO:1) of the 5' region of TobRD2.

DETAILED DESCRIPTION OF THE INVENTION

Figure 1A:
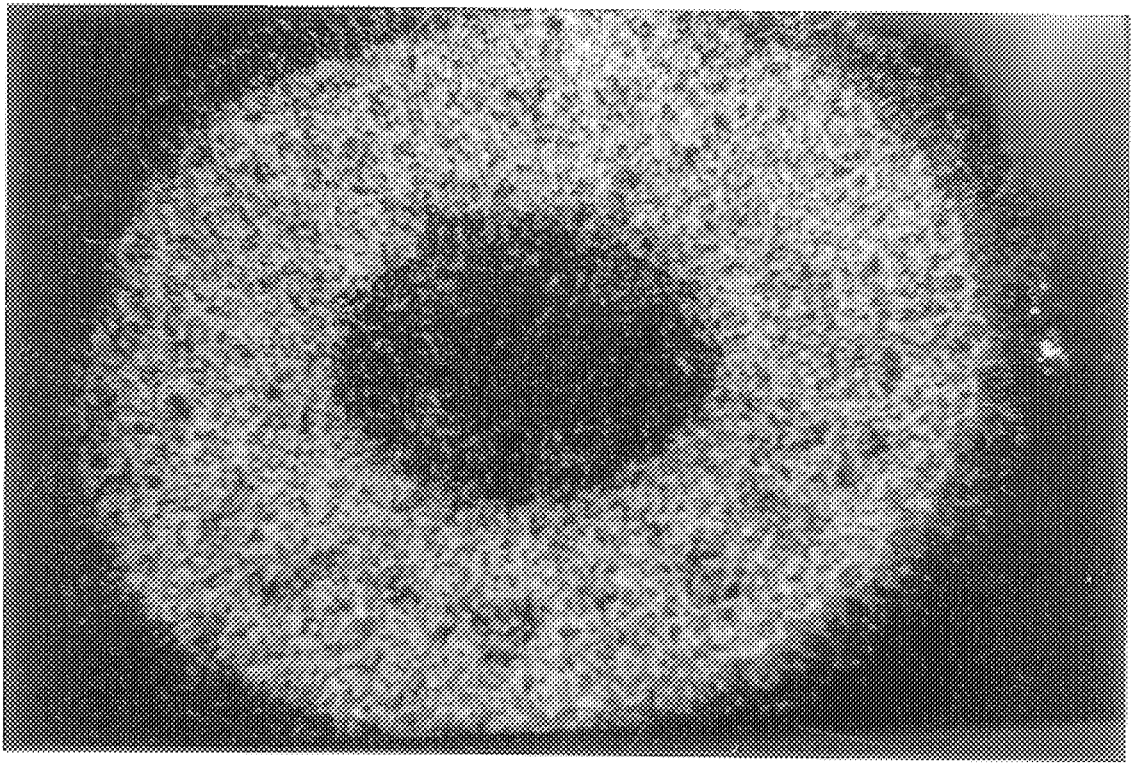
FIG. 1A shows in situ localization of Tobacco RD2 transcripts in a transverse section of tobacco root from a seven day old seedling.

Nucleotide sequences are presented herein by single strand only, in the 5' to 3' direction, from left to right. Nucleotides are represented herein in the manner recommended by the IUPAC-IUB Biochemical Nomenclature Commission.

Transgenic plants expressing peptides that inhibit or kill a particular pest or pathogen provide a method for decreasing crop damage and loss. For example, expression of the *Bacillus thuringiensis* protein in transgenic corn provides resistance to the European corn bore. However, transgene expression in all tissues of a plant (constitutive expression) is disadvantageous as it can expose non-target organisms to the transgenic protein and in addition increases the selective pressure for the development of pathogens and pests which are resistant to the transgenic protein. High levels of transgene expression throughout a plant may also negatively affect growth and yield of the plant. An alternative strategy is to express a toxic peptide only in the organ or tissue affected by a particular pest or pathogen. Implementation of this strategy against pests and pathogens that attack plant roots has been hampered by the lack of characterized root-specific promoters.

Transcription of a gene is initiated when a stable complex is formed between RNA polymerase enzyme and a gene promoter. Promoters occur at the beginning of all transcription units, are typically about 100 base pairs in length, and are located immediately upstream from the start site of transcription. See e.g., Maniatis et al., *Science* 236:1238 (1987). Promoters vary in their 'strength', that is, in their ability to accurately and efficiently initiate transcription. The RNA polymerase holoenzyme is thought to cover a region of about 50 bases immediately upstream of the transcribed region. In some cases the strength of transcription initiation may be enhanced by auxiliary proteins that bind adjacent to the region of the promoter which is immediately upstream from the transcribed DNA. See, e.g., Singer & Berg, *Genes and Genomes*, 140–145, University Science Books, Mill Valley, Caiff. (1991).

Specific examples of root cortex specific promoters of the present invention are DNA molecules which have a sequence corresponding to any one of those shown in SEQ ID NOS: 1–9, all of which are discussed in greater detail below. It will be apparent that other sequence fragments from the Tobacco RD2 5' flanking region, longer or shorter than the foregoing sequences, or with minor additions, deletions, or substitutions made thereto, can be prepared which will also carry the TobRD2 root cortex specific promoter, all of which are included within the present invention. A further aspect of the present invention includes promoters isolated from other tobacco genes, or from plants other than tobacco as set forth below, which are homologous to the tobacco RD2 promoter and are capable of directing root cortex specific transcription of a downstream heterologous DNA segment in a plant cell.

As used herein, a TobRD2 promoter refers to a DNA molecule having a sequence identical to, or substantially homologous to, a continuous segment of the DNA found 5' to the transcribed region of the tobacco RD2 gene. SEQ ID NO:1 given herein provides the sequence of the 2 kb region found immediately 5' to the initiation of transcription in the TobRD2 gene. TobRD2 promoters include the at least 100 base pair region, the 150 base pair region, or preferably the 200 base pair region immediately 5' to the TobRD2 transcribed region, and direct root cortex specific expression. As used herein, regions that are 'substantially homologous' are at least 75%, and more preferably are 80%, 85%, 90% or even 95% homologous.

As used herein, a root cortex specific promoter is a promoter that preferentially directs expression of an operatively associated gene in root cortex tissue, as compared to expression in leaf or stem tissue, or other tissues of the root.

Root cortex specific promoter sequences from other plants include those which are at least about 75 percent homologous (and more preferably 80%, 85%, 90% or even 95% homologous) to the approximately 100 base segment of the Tobacco RD2 promoter immediately upstream of the transcribed DNA region, and which are capable of directing root cortex specific transcription of a downstream heterologous DNA segment in a plant cell. Root cortex specific promoters from other plants include those which are at least about 75 percent homologous (and more preferably 80%, 85%, 90% or even 95% homologous) to the continuous portions of the TobRD2 promoter as defined herein by SEQ ID NOS: 1–9, and which are capable of directing root cortex specific transcription of a downstream heterologous DNA segment in a plant cell.

High stringency hybridization conditions which will permit homologous DNA sequences to hybridize to a DNA sequence as given herein are well known in the art. For example, hybridization of such sequences to DNA disclosed herein may be carried out in 25% formamide, 5× SSC, 5× Denhardt's solution, with 100 μg/ml of single stranded DNA and 5% dextran sulfate at 42° C., with wash conditions of 25% formamide, 5× SSC, 0.1% SDS at 42° C. for 15 minutes, to allow hybridization of sequences of about 60% homology. More stringent conditions are represented by a wash stringency of 0.3M NaCl, 0.03M sodium citrate, 0.1% SDS at 60 ° or even 70° C. using a standard in situ hybridization assay. (See Sambrook et al., *Molecular Cloning, A Laboratory Manual* (2d Ed. 1989)(Cold Spring Harbor Laboratory)). In general, plant DNA sequences which code for root cortex specific promoters and which hybridize to the DNA sequence encoding the tobacco RD2 root cortex specific promoters disclosed herein will be at least 75%, 80%, 85%, 90% or even 95% homologous or more with the sequences of the DNA encoding the tobacco RD2 root cortex specific promoters disclosed herein.

Root cortex specific promoters of the present invention are useful in directing tissue specific expression of transgenes in transformed plants. Such tissue-specific transgene expression is useful in providing resistance against damage caused by pests and pathogens which attack plant roots. In addition, as the root cortex is a major sink organ for photosynthate storage, expression of transgenes designed to alter the stored carbohydrates may be directed by such promoters. Exogenous genes of particular interest for root-cortex specific expression include those that code for proteins that bind heavy metals (such as metallothionein) ; proteins that give resistance to soil borne pests and pathogens; proteins that confer resistance to heat, salt (salinity) and drought; proteins for desalinization; and proteins that metabolize plant storage compounds into alternative preferred products or forms.

Tissue specific promoters may also be used to convert pro-pesticides to active forms in selected tissue sites. Hsu et al. *Pestic. Sci.*, 44, 9 (1995) report the use of a chimeric gene comprising the root-specific promoter TobRB7 and the β-glucuronidase enzyme gene, to preferentially convert a pro-pesticide to an active form in roots. The inactive pro-pesticide (a glucuronide of hydroxymethyloxamyl) was applied to foliage and was then transported through plant phloem to roots, where it was converted to an active nematocidal form by glucuronidase.

Additionally, root-cortex specific promoters are useful for histological purposes, to identify or stain root-cortex tissue using a reporter gene such as β-glucurodinase.

The term "operatively associated," as used herein, refers to DNA sequences contained within a single DNA molecule which are associated so that the function of one is affected by the other. Thus, a promoter is operatively associated with a gene when it is capable of affecting the expression of that gene (i.e., the gene is under the transcriptional control of the promoter). The promoter is said to be "upstream" from the gene, which is in turn said to be "downstream" from the promoter.

DNA constructs, or "expression cassettes," of the present invention include, 5'–3' in the direction of transcription, a promoter of the present invention, a heterologous DNA segment operatively associated with the promoter, and, optionally, transcriptional and translational termination regions such as a termination signal and a polyadenylation region. All of these regulatory regions should be capable of operating in the transformed cells. The 3' termination region may be derived from the same gene as the transcriptional initiation region or from a different gene.

Plants may be divided into those lacking chlorophyll (such as fungi) and those containing chlorophyll (such as green algae, mosses) ; and further divided into those containing chlorophyll and having vascular tissue (such as ferns, gymnosperms, conifers, monocots and dicots). The latter group of plants includes those in which roots, stems and leaves may be present. As used herein, the term 'plant' encompasses all such organisms described above. As used herein, the term 'natural plant DNA' means DNA isolated from non-genetically altered, or untransformed, plants (for example, plant varieties which are produced by selective breeding).

As used herein, the term heterologous gene or heterologous DNA segment means a gene (or DNA segment) which is used to transform a cell by genetic engineering techniques, and which may not occur naturally in the cell. Structural genes are those portions of genes which comprise a DNA segment coding for a protein, polypeptide, or portion thereof, possibly including a ribosome binding site and/or a translational start codon, but lacking a promoter. The term can also refer to copies of a structural gene naturally found within a cell but artificially introduced. Structural genes may encode a protein not normally found in the plant cell in which the gene is introduced or in combination with the promoter to which it is operationally associated. Genes which may be operationally associated with a promoter of the present invention for expression in a plant species may be derived from a chromosomal gene, cDNA, a synthetic gene, or combinations thereof. As used herein, the term heterologous DNA segment also includes DNA segments coding for non-protein products, such as ribozymes or anti-sense RNAs. Antisense RNAs are well known (see, e.g., U.S. Pat. No. 4,801,540 (Calgene, Inc.)).

Genes of interest for use with the present invention in plants include those affecting a wide variety of phenotypic and non-phenotypic properties. Among the phenotypic properties are proteins, such as enzymes, which provide resistance to various environmental stresses, including but not limited to stress caused by dehydration (resulting from heat, salinity or drought), herbicides, toxic metals, trace elements, pests and pathogens. Resistance may be due to a change in the target site, enhancement of the amount of a target protein in the host cell, increased amounts of one or more enzymes involved with the biosynthetic pathway of a product which protects the host against the stress, and the like. Structural genes may be obtained from prokaryotes or eukaryotes, bacteria, fungi, (e.g., from yeast, viruses, plants, and mammals) or may be synthesized in whole or in part. Illustrative genes include glyphosphate resistant 3-enolpyruvylphosphoshikinate synthase gene, nitrilase, genes in the proline and glutamine biosynthetic pathway, and metallothioneins.

Structural genes operatively associated with the promoter of the present invention may be those which code for a protein toxic to insects, such as a *Bacillus thuringiensis* crystal protein toxic to insects. A DNA sequence encoding a *B. thuringiensis* toxin toxic to Coleoptera, and variations of this sequence wherein the coded-for toxicity is retained, is disclosed in U.S. Pat. No. 4,853,331 (see also U.S. Pat. Nos. 4,918,006 and 4,910,136)(the disclosures of all U.S. Patent references cited herein are to be incorporated herein in their entirety by reference). A gene sequence from *B. thuringiensis* which renders plant species toxic to Lepidoptera is disclosed in PCT Application WO 90/02804. PCT Application WO 89/04868 discloses transgenic plants transformed with a vector which promotes the expression of a *B. thuringiensis* crystal protein, the sequence of which may be employed in connection with the present invention. PCT Application WO 90/06999 discloses DNA encoding a *B. thuringiensis* crystal protein toxin active against Lepidoptera. Another gene sequence encoding an insecticidal crystal protein is disclosed in U.S. Pat. No. 4,918,006. Exemplary of gene sequences encoding other insect toxins are gene sequences encoding a chitinase (e.g., EC-3.2.1.14), as disclosed in U.S. Pat. No. 4,940,840 and PCT Appln. No. WO 90/07001. A gene coding for a nematode-inducible pore protein useful in producing transgenic plants resistant to root nematodes is disclosed in U.S. Pat. application Ser. No. 08/007,998. Strains of *B. thuringiensis* which produce polypeptide toxins active against nematodes are disclosed in U.S. Pat. Nos. 4,948,734 and 5,093,120 (Edwards et al.).

Where the expression product of the gene is to be located in a cellular compartment other than the cytoplasm, the structural gene may be constructed to include regions which code for particular amino acid sequences which result in translocation of the product to a particular site, such as the cell plasma membrane, or secretion into the periplasmic space or into the external environment of the cell. Various secretory leaders, membrane integration sequences, and translocation sequences for directing the peptide expression product to a particular site are described in the literature. See, for example, Cashmore et al., *Biotechnology* (1985) 3:803–808, Wickner and Lodish, *Science* (1985) 230:400–407.

The expression cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there may be at least one marker present, which may be useful in one or more hosts, or different markers for individual hosts. That is, one marker may be employed for selection in a prokaryotic host while another marker may be employed for selection in a eukaryotic host, particularly the plant host. The markers may provide protection against a biocide, such as antibiotics, toxins, heavy metals, or the like; may provide complementation by imparting prototrophy to an auxotrophic host; or may provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase (GUS) (providing indigo production), luciferase (providing visible light production), NPTII (providing kanamycin resistance or G418 resistance), HPT (providing hygromycin resistance), and the mutated aroA gene (providing glyphosate resistance).

The various fragments comprising the various constructs, expression cassettes, markers, and the like may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature. See, e.g., Maniatis et al., *Molecular Cloning: A Laboratory Manual*, Cold Spring Harbor Laboratory, Cold Spring Harbor, N.Y. (1982).

A vector is a replicable DNA construct. Vectors which may be used to transform plant tissue with DNA constructs of the present invention include both Agrobacterium vectors and ballistic vectors, as well as vectors suitable for DNA-mediated transformation. *Agrobacterium tumefaciens* cells containing a DNA construct of the present invention, wherein the DNA construct comprises a Ti plasmid, are useful in methods of making transformed plants. Plant cells are infected with an *Agrobacterium tumefaciens* to produce a transformed plant cell, and then a plant is regenerated from the transformed plant cell.

Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T-DNA region, and a second plasmid having a T-DNA region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Agracetus European Patent Application Publication No. 0 270 356, titled "Pollen-mediated Plant Transformation". When using ballistic transformation procedures, the expression cassette may be incorporated into a plasmid capable of replicating in the cell to be transformed. Examples of microparticles suitable for use in such systems include 1 to 5 $\mu$m gold spheres. The DNA construct may be deposited on the microparticle by any suitable technique, such as by precipitation.

A transformed host cell is a cell which has been transformed or transfected with constructs containing a DNA sequence as disclosed herein using recombinant DNA techniques. Plant species may be transformed with the DNA construct of the present invention by the DNA-mediated transformation of plant cell protoplasts and subsequent regeneration of the plant from the transformed protoplasts in accordance with procedures well known in the art.

The promoter sequences disclosed herein may be used to express a heterologous DNA sequence in any plant species capable of utilizing the promoter (i.e., any plant species the RNA polymerase of which binds to the promoter sequences disclosed herein). Examples of plant species suitable for transformation with the DNA constructs of the present invention include both monocots and dicots, and include but are not limited to tobacco, soybean, potato, cotton, sugarbeet, sunflower, carrot, celery, flax, cabbage and other cruciferous plants, pepper, tomato, citrus trees, bean, strawberry, lettuce, maize, alfalfa, oat, wheat, rice, barley, sorghum and canola. Thus an illustrative category of plants which may be transformed with the DNA constructs of the present invention are the dicots, and a more particular category of plants which may be transformed using the DNA constructs of the present invention are members of the family Solanacae.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

The examples which follow are provided to illustrate various specific embodiments of the present invention, and are not to be construed as limiting the invention.

EXAMPLE 1

Isolation of Genomic Root Cortex Specific RD2 Genes

A tobacco (*Nicotania tabacum*) genomic library of DNA isolated from tobacco seedlings was constructed in EMBL 3 SP6/T7 lambda vector (ClonTech, Palo Alto, Cailf.). TobRD2 cDNA (Conkling et al., *Plant Phys.* 93, 1203 (1990)) was used as a probe to isolate genomic clones containing Tobacco RD2 genes from the primary library. A total of $1.2 \times 10^7$ recombinant phage were screened on K802 bacterial cells. The plaques were lifted onto nylon membranes (Magnagraph), and the DNA immobilized by autoclaving (10 minutes, gravity cycle). All hybridizations were performed at 65° C. in aqueous solution (5× SSC [750 mM sodium chloride, 75 mM sodium citrate], 5× Denhardt's [0.1% each of ficoll, BSA, polyvinylpyrolidone], 0.5% SDS, 100 mg/ml denatured salmon sperm DNA) for 16 hours. The filters were washed in 0.2× SSC and 0.1% SDS at 60° C.

Thirteen genomic clones that hybridized to the TobRD2 cDNA probe were identified by screening $1.2 \times 10^7$ recombinant phage. These clones were isolated and further characterized by restriction mapping. Restriction maps were constructed by the rapid mapping procedure of Rachwitz et al., *Gene,* 30:195 (1984). One clone, homologous to the TobRD2 cDNA, was sequenced in its entirety and its promoter identified. By aligning the TobRD2 cDNA and the genomic clone, the region of the genomic clone 5' to the translated region was identified. The sequence of this untranslated region was examined and the TATAA box of the putative promoter was identified. In plant promoters, the TATAA box is typically −35 to −29 nucleotides from the initiation point of transcription. Using primer extension experiments, the 5' end of transcription was identified.

A 2010 base pair region upstream from the transcribed region of the TobRD2 cDNA is provided in FIG. 2 (SEQ ID NO:1). This sequence includes the predicted start of the transcription region (at nucleotide 2000), and the TATAA box of the promoter (nucleotides 1971–1975).

EXAMPLE 2

Nucleic Acid Sequencing Restriction fragments from the isolated genomic clones (Example 1) were subcloned into bluescript (pBS KS II + or pBS SK II+; Stratagene, La Jolla, Cailf.) vectors. Unidirectional deletion series was obtained for each clone and for both DNA strands by Exonuclease III and S1 nuclease digestion (Henikoff, *Gene* 28, 351 (1984). The DNA sequence was determined by dideoxy chain-termination method (Sanger et al., *Proc. Natl. Acad. Sci. USA,* 74, 5463 (1977)) using the enzyme Sequenase (U.S. Biochemicals, Cleveland, Ohio) In all cases, both DNA strands were sequenced.

EXAMPLE 3

In-Situ Hybridizations

To determine the spatial distribution of TobRD2 mRNA transcripts in the various tissues of the root, in situ hybridizations were performed in untransformed plants. In-situ hybridizations of antisense strand of TobRD2 to the TobRD2 mRNA in root tissue was done using techniques as described in Meyerowitz, *Plant Mol. Biol.* Rep. 5,242 (1987) and Smith et al., *Plant Mol. Biol. Rep.* 5, 237 (1987). Seven day old tobacco (*Nicotania tabacum*) seedling roots were fixed in phosphate-buffered glutaraldehyde, embedded in Paraplast Plus (Monoject Inc., St. Louis, Mo.) and sectioned at 8 mm thickness to obtain transverse as well as longitudinal sections. Antisense TobRD2 transcripts, synthesized in vitro in the presence of 35S-ATP, were used as probes. The labeled RNA was hydrolyzed by alkaline treatment to yield 100 to 200 base mass average length prior to use.

Hybridizations were done in 50% formamide for 16 hours at 42° C., with approximately $5 \times 10^6$ counts-per-minute (cpm) labeled RNA per milliliter of hybridization solution. After exposure, the slides were developed and visualized under bright and dark field microscopy.

Figure 1B:
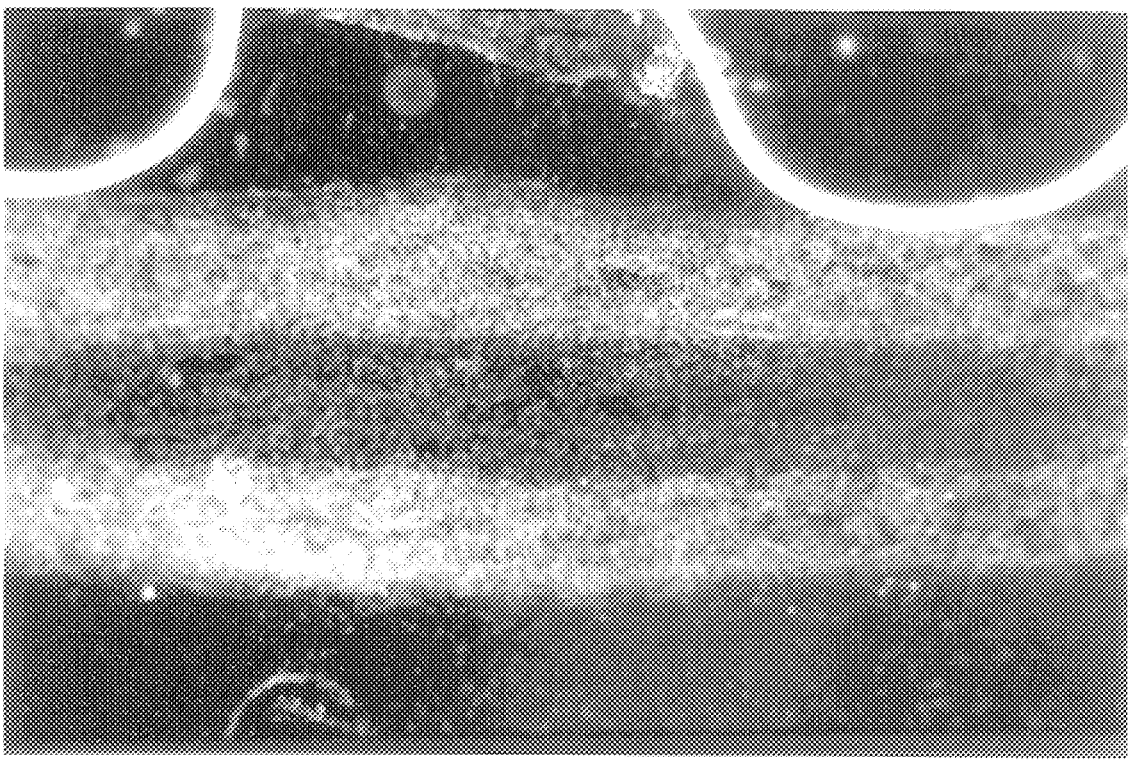
FIG. 1B shows in situ localization of Tobacco RD2 transcripts in a longitudinal section of tobacco root from a seven day old seedling.

As shown in FIGS. 1A and 1B, the hybridization signal is localized to the cortical layer of cells in the roots. Comparison of both bright and dark field images of the same sections localizes TobRD2 transcripts to the parenchymatous cells of the root cortex. No hybridization signal was visible in the epidermis or the stele.

EXAMPLE 4

Chimeric Gene Construction

A promoter deletion series was constructed by polymerase chain reaction (PCR). The templates were the various deletions of the 5' flanking regions of the TobRD2 genomic clone that had been generated by Exonuclease III/S1 nuclease digestions (Example 2).

All templates were amplified using the same set of oligonucleotide primers. One primer was a modified bacteriophage M13 forward primer (see, e.g., Sanger et al., *Proc. Natl. Acad. Sci. USA,* 74, 5463 (1977)); the 5' end of the oligonucleotide contained the HindIII recognition sequence, along with an additional 5' sequence that allows for more efficient cleavage by the restriction enzyme. The other primer was designed to have a BamHI site (along with additional nucleotides for efficient cleavage) at its 5' end and was homologous to the 16 nucleotide sequence of the TobRD2 that is found 22 bases 5' to the ATG start codon (i.e., the primer was homologous bases 1973–1988 of SEQ ID NO:1).

The PCR amplification reaction contained template plasmid DNA (5–10 ng); reaction buffer (50 mM KCl, 10 mM Tris-HCl, pH 9.0 [at 25° C.], 0.1% Triton X-100, 1.5 mM MgCl); 0.25 mM each of DATP, dGTP, dTTP, and dCTP; 40 ng of each primer; 1.25 units of Taq DNA polymerase (Promega, Madison, Wis.).

The PCR cycle denatured the templates at 94° C. for 1 minute, annealed the primers at 46° C. for 1 minute and allowed chain elongation to proceed at 72° C. for 5 minutes. This cycle was repeated 40 times and the last elongation cycle was extended by 10 minutes. PCR amplifications were done in a programmable thermal cycler (PTC-100, M.J. Research).

Amplified products were digested with Hind III and Bam HI and cloned into the Hind III and Bam HI sites of the Agrobacterium binary vector pBI 101.3 (R. Jefferson et al., EMBO J. 6, 3901–3907 (1987)). This vector contains a β-glucuronidase (GUS) reporter gene and an nptII selectable marker flanked by the T-DNA border sequences.

EXAMPLE 5

Plant Transformation: Methods

Chimeric reporter gene constructs were introduced into an Agrobacterium host carrying a disarmed Ti-plasmid (LBA4404) capable of providing (in trans) the vir functions required for T-DNA transfer and integration into the plant genome, essentially as described by An et al., in S. Belvin and R. Schilperoot, eds., *Plant Molecular Biology Manual*, Martinus Nijhoff, Dordrecht, The Netherlands, pp A3-1–19 (1988). Constructs were introduced to the host via tri-parental mating or electroporation of electrocompetent Agrobacterium cells, as is known to those in the art. Leaf disc transformation of tobacco (SR1) and plant regeneration were performed as described by An et al. *Plant Physiol.* 81, 301–305 (1986). Kanamycin resistant plants were selected for further analysis.

EXAMPLE 6

GUS Assays in Transgenic Plants: Methods

Histochemical staining was performed on excised roots, stems and leaves of transformed plants. The explant tissues were incubated in 1 mM 5-bromo-4-chloro-3-indolyl-B-D-glucuronide (X-Gluc), 25 mM sodium phosphate buffer (pH 7.0), 0.5% DMSO, at 37° C. overnight after briefly vacuum infiltrating the substrate. Tissues expressing GUS activity cleave this substrate and thereby stain blue.

Flurometric GUS assays were performed as described by Jefferson et al., *EMBO J.* 6, 3901–3907 (1987) to quantitate the level of GUS expression. Cell extracts from roots, leaves and stems were incubated in the presence of 1 mM 4-methylumbelliferyl-B-D-glucuronide (MUG) at 37° C. Samples were taken at 0, 5, 10, 15, and 20 minute intervals. The enzyme reaction was stopped by the addition of 0.2M sodium carbonate. The fluorometer was calibrated with 10 nM and 100 nM MUG. Protein concentration in the samples was determined according the method of Bradford, *Anal. Diochem.* 72, 248 (1976).

EXAMPLE 7

Chimeric gene construct is capable of directing tissue-specific gene expression To determine if the 2010 base pair sequence from the TobRD2 gene (SEQ. ID NO:1) encompassed promoter elements directing expression specifically in the parenchymatous cells of the root cortex, chimeric genes were constructed. A 1988 base pair region (SEQ ID NO:2) was amplified by polymerase chain reaction and cloned 5' to the GUS reporter gene (as described above). The chimeric gene was introduced into tobacco (as described above) and transgenic plants were analyzed for their ability to express GUS (as described above).

Figure 4:
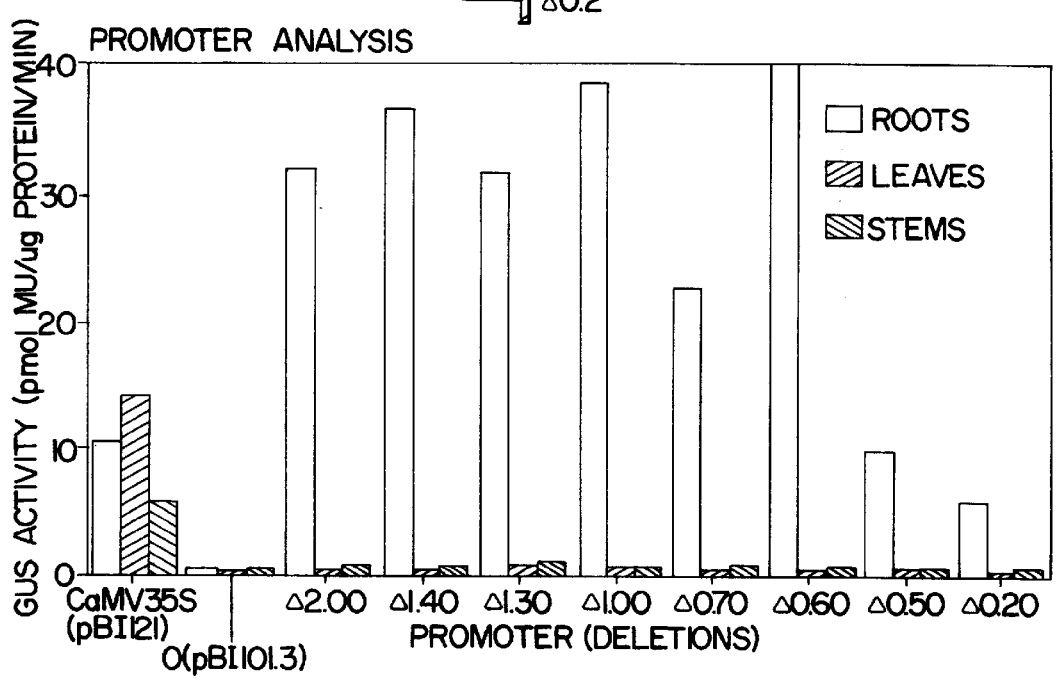
FIG. 4 is a bar graph summarizing β-glucurodinase (GUS) activity in roots (solid bars), leaves (stippled bars) and stems (dotted bars) of plants transformed with chimeric reporter gene constructs, as provided in Table 1. The graph shows activity among plants transformed with gene constructs utilizing different promoters (CaMV35S; Δ2.00; Δ1.50; Δ1.40; Δ1.25; Δ0.80; Δ0.70; Δ0.60; Δ0.30) and utilizing the vector pBI101.3 alone as a control. GUS activity was measured in pmolMU/μg protein/min.

Results of the analysis of 9 individual transformants (i.e., each transformant was the product of an independent transforming event) are shown in Table 1, lines 25–33 (transformants 325II1–325IV5). The Δ2.0 promoter (SEQ ID NO:2) was found to direct high levels of gene expression (approximately 4-fold higher than that of the CaMV35S promoter, commonly termed to be a 'strong' promoter) (FIG. 4). Expression of the reporter could not be detected in leaves or stems at levels higher than control (see FIGS. 4, 5A and 5B, which display average activities taken from Table 1). GUS activity was essentially limited to the root and, as shown in FIG. 6, was specifically limited to the root cortex. The plant shown in FIG. 6 was transformed using the Δ2.0 promoter driving GUS, in pBI101.3.

Multiple individual transformed leaf disks were placed in petri plates. Transformant nomenclature in Table 1 indicates the promoter/the numbered petri plate/and the number of the independent transformant. Thus 325II1 refers to a transformant using the Δ2.0 promoter, in petri plate II, and from leaf disc 1; while 101.I1 refers to transformation using pBI101.3 (promoterless GUS used as a control), and to transformant number 1 in petri plate I. In Table 1, the prefix 121 refers to use of pBI121 (CaMV35S promoter with GUS); 325 refers to the Δ2.0 promoter (SEQ ID NO:2) with GUS; 484 refers to the Δ1.4 promoter (SEQ ID NO:3) with GUS; 421 refers to the Δ1.3 promoter (SEQ ID NO:4) with GUS; 428 refers to the Δ1.0 promoter (SEQ ID NO:5) with GUS; 490 refers to the Δ0.7 promoter (SEQ ID NO:6) with GUS; 491 refers to the Δ0.6 promoter (SEQ ID NO:7) with GUS; 492 refers to the Δ0.5 promoter (SEQ ID NO:8) with GUS; 495 refers to the Δ0.2 promoter (SEQ ID NO:9) with GUS. "R-GUS" refers to GUS activity in root tissues; "L-GUS" refers to GUS activity in leaf tissues; and "S-GUS" refers to GUS activity in stem tissues. R/L provides the relative GUS activity in Roots/Leaves; R/S provides the relative GUS activity in Roots/Stems. GUS activity is provided in pmolMU/μg protein/min.

TABLE 1

TOBRD2 PROMOTER ANALYSIS

| Transformants | R-GUS activity | Average | L-GUS activity | Average | S-GUS activity | Average | R/L | R/L mean | R/S | R/S mean |
|---|---|---|---|---|---|---|---|---|---|---|
| 101.I1   | 0.19  | 0.56  | 0.23  | 0.33  | 0.22  | 0.36 | 0.83 | 1.67 | 0.86 | 1.51 |
| 101.I2   | 0.12  |       | 0.14  |       | 0.15  |      | 0.86 |      | 0.80 |      |
| 101.I3   | 0.13  |       | 0.35  |       | 0.32  |      | 0.37 |      | 0.41 |      |
| 101.I4   | 0.73  |       | 0.46  |       | 0.24  |      | 1.59 |      | 3.04 |      |
| 101.II1  | 0.44  |       |       |       | 0.31  |      |      |      | 1.42 |      |
| 101.II3  | 0.59  |       | 0.23  |       | 0.47  |      | 2.57 |      | 1.26 |      |
| 101.II4  | 0.86  |       | 0.41  |       | 0.34  |      | 2.10 |      | 2.53 |      |
| 101.II5  | 0.64  |       | 0.36  |       | 0.33  |      | 1.78 |      | 1.94 |      |
| 101.III1 | 0.69  |       | 0.24  |       | 0.42  |      | 2.88 |      | 1.64 |      |
| 101.III3 | 0.25  |       | 0.19  |       | 0.21  |      | 1.32 |      | 1.19 |      |
| 101.III4 | 0.71  |       | 0.37  |       | 0.27  |      | 1.92 |      | 2.63 |      |
| 101.III5 | 0.15  |       | 0.13  |       | 0.21  |      | 1.15 |      | 0.71 |      |
| 101.IV1  | 0.21  |       | 0.10  |       | 0.13  |      | 2.10 |      | 1.62 |      |
| 101.IV2  | 0.27  |       | 0.24  |       | 0.23  |      | 1.13 |      | 1.17 |      |
| 101.IV3  | 0.88  |       | 0.42  |       | 0.57  |      | 2.10 |      | 1.54 |      |
| 101.IV4  | 0.75  |       | 0.35  |       | 0.67  |      | 2.14 |      | 1.12 |      |
| 101.IV5  | 1.88  |       | 0.98  |       | 1.02  |      | 1.92 |      | 1.84 |      |
| 121.I5   | 3.00  | 10.50 | 3.65  | 14.36 | 2.25  | 5.81 | 0.82 | 0.71 | 1.33 | 1.69 |
| 121.IV1  | 24.67 |       | 30.79 |       | 11.96 |      | 0.80 |      | 2.06 |      |

TABLE 1-continued

TOBRD2 PROMOTER ANALYSIS

| Transformants | R-GUS activity | Average | L-GUS activity | Average | S-GUS activity | Average | R/L | R/L mean | R/S | R/S mean |
|---|---|---|---|---|---|---|---|---|---|---|
| 121.IV2 | 9.20 | | 11.66 | | 5.33 | | 0.79 | | 1.73 | |
| 121.IV4 | 12.13 | | 15.61 | | 7.42 | | 0.78 | | 1.63 | |
| 121.4 | 3.50 | | 10.10 | | 2.08 | | 0.35 | | 1.68 | |
| 325II1 | 35.30 | 32.15 | 0.54 | 0.46 | 0.61 | 0.78 | 65.37 | 67.19 | 57.87 | 50.17 |
| 325II2 | 24.94 | | 0.24 | | 0.35 | | 103.92 | | 71.26 | |
| 325II4 | 13.64 | | 0.17 | | 0.23 | | 80.24 | | 59.30 | |
| 325II5 | 38.09 | | | | 0.64 | | | | 59.52 | |
| 325III1 | 45.31 | | 0.38 | | | | | | | |
| 325III2 | 34.05 | | 0.44 | | | | | | | |
| 325III5 | 55.81 | | 0.76 | | 0.77 | | 73.43 | | 72.48 | |
| 325IV1 | 16.51 | | 0.68 | | 0.94 | | 24.28 | | 17.56 | |
| 325IV5 | 25.71 | | 0.46 | | 1.95 | | 55.89 | | 13.18 | |
| 484I1 | 61.75 | 36.68 | | 0.46 | | 0.67 | | 74.41 | | 53.68 |
| 484I3 | 59.72 | | | | | | | | | |
| 484I4 | 72.35 | | | | | | | | | |
| 484I5 | 56.58 | | | | | | | | | |
| 484V2 | 38.32 | | 0.78 | | 0.86 | | 49.13 | | 44.56 | |
| 484V3 | 23.66 | | 0.31 | | 2.29 | | 76.32 | | 10.33 | |
| 484III3 | 63.28 | | | | | | | | | |
| 484III4 | 42.91 | | 0.87 | | 0.98 | | 49.32 | | 43.79 | |
| 484II4 | 15.80 | | 0.43 | | 0.27 | | 36.74 | | 58.52 | |
| 484V4 | 58.25 | | 0.46 | | 0.48 | | 126.63 | | 121.35 | |
| 484V1 | 26.86 | | 0.81 | | 1.27 | | 33.16 | | 21.15 | |
| 484V5 | 8.53 | | 0.42 | | 0.34 | | 20.31 | | 25.09 | |
| 484IV5 | 17.83 | | 0.51 | | 0.29 | | 34.96 | | 61.48 | |
| 484IV3 | 14.05 | | 0.35 | | 0.34 | | 40.14 | | 41.32 | |
| 484IV2 | 32.33 | | 0.32 | | 0.51 | | 101.03 | | 63.39 | |
| 484II3 | 10.18 | | 0.13 | | 0.16 | | 78.31 | | 63.63 | |
| 484II5 | 33.51 | | 0.55 | | 0.63 | | 60.93 | | 53.19 | |
| 484II2 | 52.54 | | 0.43 | | 0.79 | | 122.19 | | 66.51 | |
| 484II1 | 8.50 | | 0.04 | | 0.11 | | 212.50 | | 77.27 | |
| 421IV4 | 25.04 | 31.87 | 0.82 | 0.81 | 2.27 | 1.01 | 30.54 | 40.54 | 11.03 | 36.78 |
| 421V4 | 46.31 | | 0.82 | | | | 56.48 | | | |
| 421II4 | 79.23 | | 0.96 | | 1.89 | | 82.53 | | 41.92 | |
| 421III3 | 17.00 | | 0.45 | | 1.09 | | 37.78 | | 15.60 | |
| 421II3 | 19.07 | | 0.42 | | 0.37 | | 45.40 | | 51.54 | |
| 421I1 | 27.67 | | 0.72 | | 0.64 | | 38.43 | | 43.23 | |
| 421I3 | 74.45 | | 2.27 | | 1.44 | | 32.80 | | 51.70 | |
| 421II2 | 43.36 | | 0.88 | | 0.56 | | 49.27 | | 77.43 | |
| 421I4 | 8.41 | | | | | | | | | |
| 421V1 | 32.32 | | 0.94 | | 1.34 | | 34.38 | | 24.12 | |
| 421V2 | 5.07 | | 0.43 | | 0.13 | | 11.79 | | 39.00 | |
| 421IV3 | 4.52 | | 0.17 | | 0.37 | | 26.59 | | 12.22 | |
| 428I5 | 20.62 | 38.64 | 0.98 | 0.66 | 0.83 | 0.65 | 21.04 | 72.65 | 24.84 | 47.43 |
| 428I2 | 15.05 | | 0.97 | | 0.25 | | 15.52 | | 60.20 | |
| 428III3 | 69.87 | | 1.10 | | | | 63.52 | | | |
| 428III1 | 30.97 | | 0.52 | | 0.36 | | 59.56 | | 86.03 | |
| 428V2 | 54.66 | | 0.24 | | | | 227.75 | | | |
| 428V1 | 85.71 | | 0.98 | | 1.25 | | 87.46 | | 68.57 | |
| 428IV4 | 4.15 | | | | 0.29 | | | | 14.31 | |
| 428IV5 | 26.42 | | 0.43 | | 1.10 | | 61.44 | | 24.02 | |
| 428V3 | 1.58 | | 0.16 | | 0.17 | | 9.88 | | 9.29 | |
| 428V2 | 25.60 | | 0.34 | | | | 75.29 | | | |
| 428III5 | 90.36 | | 0.86 | | 0.98 | | 105.07 | | 92.20 | |
| 490II4 | 9.38 | 22.77 | | 0.54 | | 0.75 | | 41.65 | | 36.11 |
| 490II5 | 9.67 | | 0.35 | | 0.65 | | 27.63 | | 14.88 | |
| 490I1 | 33.62 | | 0.93 | | 2.02 | | 36.15 | | 16.64 | |
| 490I2 | 34.66 | | 0.98 | | 1.13 | | 35.37 | | 30.67 | |
| 490I3 | 4.58 | | | | | | | | | |
| 490III2 | 76.74 | | | | | | | | | |
| 490III4 | 58.75 | | 1.07 | | 1.21 | | 54.91 | | 48.55 | |
| 490III5 | 6.65 | | 0.21 | | 0.09 | | 31.67 | | 73.89 | |
| 490IV2 | 12.24 | | | | | | | | | |
| 490II1 | 8.09 | | 0.22 | | 0.21 | | 36.77 | | 38.52 | |
| 490IV4 | 20.19 | | 0.35 | | 0.52 | | 57.69 | | 38.83 | |
| 490IV5 | 17.57 | | 0.34 | | 0.57 | | 51.68 | | 30.82 | |
| 490IV3 | 18.11 | | | | | | | | | |
| 490I5 | 23.03 | | 0.78 | | 0.93 | | 29.53 | | 24.76 | |
| 490V5 | 8.27 | | 0.15 | | 0.19 | | 55.13 | | 43.53 | |
| 491I2 | 8.31 | 39.76 | | 0.50 | | 0.63 | | 53.70 | | 45.85 |
| 491II3 | 6.73 | | | | | | | | | |
| 491II4 | 13.01 | | 0.23 | | 0.19 | | 56.57 | | 68.47 | |
| 491V5 | 87.40 | | | | | | | | | |
| 491IV1 | 77.12 | | 1.02 | | 1.34 | | 75.61 | | 57.55 | |
| 491IV3 | 49.20 | | 0.98 | | 1.23 | | 50.20 | | 40.00 | |

TABLE 1-continued

TOBRD2 PROMOTER ANALYSIS

| Transformants | R-GUS activity | Average | L-GUS activity | Average | S-GUS activity | Average | R/L | R/L mean | R/S | R/S mean |
|---|---|---|---|---|---|---|---|---|---|---|
| 491III1 | 18.84 | | 0.32 | | 0.34 | | 58.88 | | 55.41 | |
| 491III2 | 30.82 | | 0.47 | | 0.58 | | 65.57 | | 53.14 | |
| 491II5 | 8.46 | | 0.28 | | .045 | | 30.21 | | 18.80 | |
| 491IV5 | 2.88 | | | | | | | | | |
| 491II5 | 8.55 | | 0.22 | | 0.31 | | 28.86 | | 27.58 | |
| 491IV4 | 165.77 | | | | | | | | | |
| 492V2 | 2.40 | 9.89 | 0.21 | 0.57 | 0.24 | 0.54 | 11.43 | 15.59 | 10.00 | 16.72 |
| 492V4 | 3.17 | | 0.27 | | 0.48 | | 11.74 | | 6.60 | |
| 492I3 | 4.40 | | 0.87 | | 0.35 | | 5.06 | | 12.57 | |
| 492I4 | 6.58 | | 0.50 | | 0.37 | | 13.16 | | 17.78 | |
| 492I5 | 10.26 | | | | | | | | | |
| 492III2 | 11.87 | | 0.78 | | 1.06 | | 15.22 | | 11.20 | |
| 492IV4 | 7.38 | | | | | | | | | |
| 492IV5 | 21.63 | | | | | | | | | |
| 492III5 | 11.39 | | 0.61 | | 0.32 | | 18.67 | | 35.59 | |
| 492IV1 | 20.38 | | 0.81 | | 0.94 | | 25.16 | | 21.68 | |
| 492II3 | 12.15 | | 0.42 | | 0.53 | | 28.93 | | 22.92 | |
| 492III1 | 7.03 | | 0.64 | | 0.58 | | 10.98 | | 12.12 | |
| 495I1 | 3.58 | 5.83 | 0.37 | 0.41 | 0.43 | 0.54 | 9.68 | 17.98 | 8.33 | 13.35 |
| 495I3 | 16.41 | | 0.59 | | 0.74 | | 27.81 | | 22.18 | |
| 495I4 | 3.20 | | 0.17 | | 0.17 | | 18.82 | | 18.82 | |
| 495I5 | 5.96 | | 0.32 | | 0.34 | | 18.63 | | 17.53 | |
| 495II2 | 8.49 | | 0.54 | | 0.52 | | 15.72 | | 16.33 | |
| 495III2 | 5.12 | | 0.40 | | 0.77 | | 12.80 | | 6.65 | |
| 495IV1 | 5.57 | | 0.21 | | 0.45 | | 26.52 | | 12.38 | |
| 495IV2 | 9.74 | | 0.75 | | 1.03 | | 12.99 | | 9.46 | |
| 495IV3 | 2.64 | | 0.14 | | 0.31 | | 18.66 | | 8.52 | |
| 495IV4 | 1.20 | | | | | | | | | |
| 495V1 | 3.67 | | | | | | | | | |
| 495V2 | 2.38 | | | | | | | | | |
| 495V3 | 7.60 | | | | | | | | | |
| 495V4 | 6.10 | | 0.56 | | 0.62 | | 10.89 | | 9.84 | |

EXAMPLE 8

Effect of 5' promoter-deletions on the expression of the reporter gene activity

Figure 3:
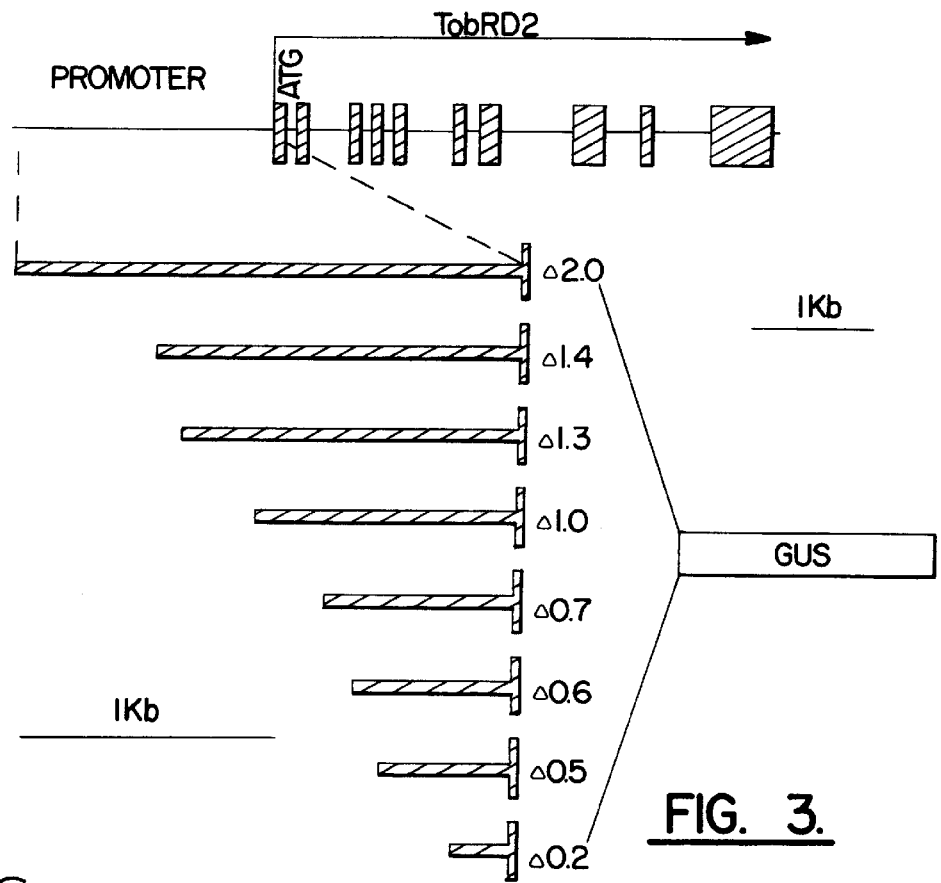
FIG. 3 is a schematic showing the TobRD2 promoter/glucurodinase (GUS) constructs used to test the ability of the RD2 promoter to direct root cortex specific gene expression.

The following experiments were carried out in essentially the same manner as described in Example 7, above, except that the length of the TobRD2 flanking region employed as a promoter was varied to explore how various portions of the flanking region affected expression of GUS A series of seven nested 5'-deletion mutations in the 2010 base pair TobRD2 sequence (SEQ ID NO:1) upstream region were generated for use as promoter sequences. These deletion mutants are shown graphically in FIG. 3, and are denoted as Δ2.0 (SEQ ID NO:2); Δ1.4 (SEQ ID NO:3) ; Δ1.3 (SEQ ID NO:4) ; Δ1.0 (SEQ ID NO:5) ; Δ0.7 (SEQ ID NO:6); Δ0.6 (SEQ ID NO:7); Δ0.5 (SEQ ID NO:8); and Δ0.2 (SEQ ID NO:9).

Chimeric gene constructs as described in Example 3 and containing the Δ2.00 promoter (SEQ ID NO:2) or a truncated promoter (SEQ ID NOs: 3–9) were introduced into tobacco by Agrobacterium mediated transformation of leaf discs (as described in Example 4). The Agrobacterium vector pBI101.3 was used alone as a control, and the CaMV35S promoter was used to provide a reference standard. Roots, leaves and stems from regenerated plants were assayed for GUS activity (Table 1; FIG. 4).

FIG. 4 provides a graphic representation of GUS activity in roots, leaves and stems using the full length TobRD2 promoter, the promoter deletion series, the Cauliflower Mosaic Virus 35S (CaMV35S) promoter, and vector pBI101.3 as a control. As shown in FIG. 4, six of the promoters tested were found to confer high levels of root cortex specific expression: Δ2.00 (SEQ ID NO:2); Δ1.4 (SEQ ID NO:3) ; Δ1.3 (SEQ ID NO:4) ; Δ1.0 (SEQ ID NO:5) ; Δ0.7 (SEQ ID NO:6); and Δ0.6 (SEQ ID NO:7). FIG. 4 displays averaged data from Table 1.

As further shown in FIG. 4, loss of a region approximately 50 base pairs in length (compare Δ0.6 (SEQ ID NO:7) and Δ0.5 (SEQ ID NO:8)) drastically decreased the level of GUS expression. However, the results show that the level of GUS expression in root tissue provided by the Δ0.5 promoter (SEQ ID NO:8) was equivalent to that elicited by the CaMV35S promoter. GUS expression in root cortex provided by the Δ0.2 promoter (SEQ ID NO:9) was approximately half that provided by the CaMV35S promoter.

Figure 5B:
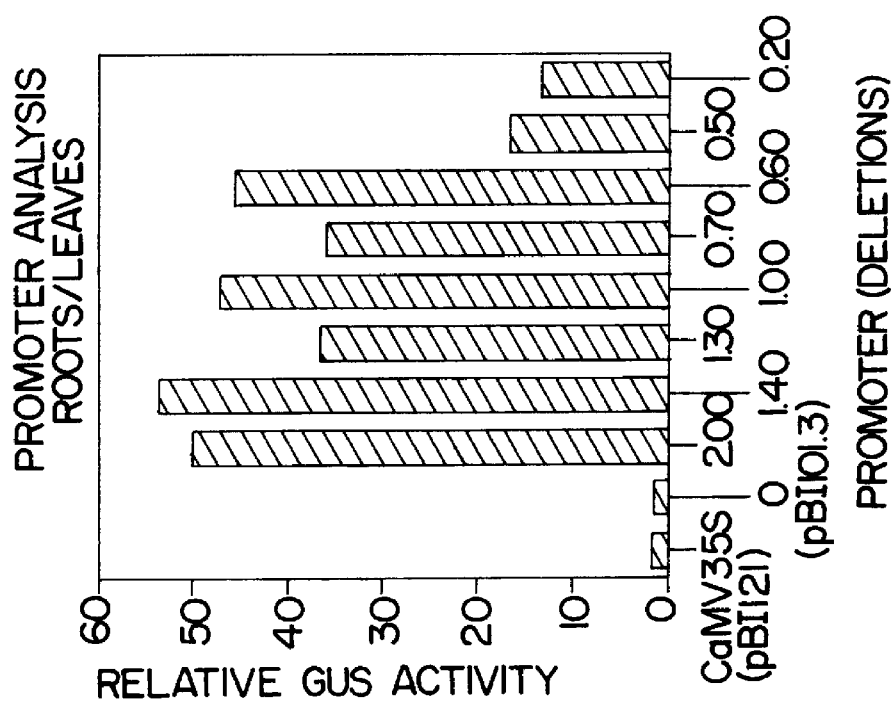
FIG. 5B is a bar graph summarizing the relative β-glucurodinase (GUS) activity in roots and stems of plants transformed with chimeric reporter gene constructs using different promoters (CaMV35S; Δ2.00; Δ1.50; Δ1.40; Δ1.25; Δ0.80; Δ0.70; Δ0.60; Δ0.30) and utilizing the vector pBI101.3 alone as a control, as provided in Table 1. GUS activity was measured in pmolMU/μg protein/min, and the relative activity shown is root activity/stem activity.
Figure 5A:
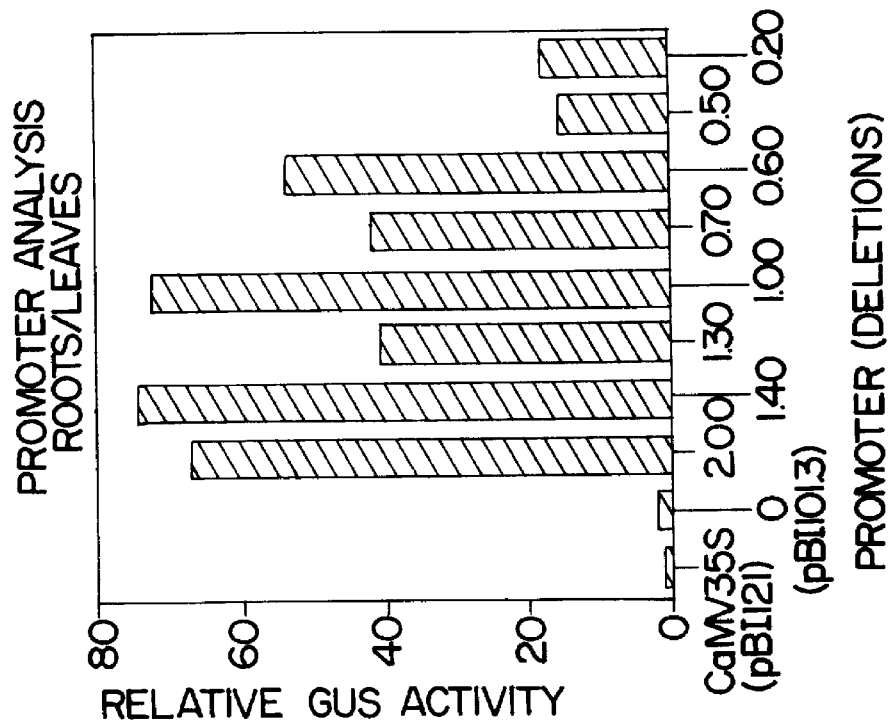
FIG. 5A is a bar graph summarizing the relative β-glucurodinase (GUS) activity in roots and leaves of tobacco plants transformed with chimeric reporter gene constructs using different promoters (CaMV35S; Δ2.00; Δ1.50; Δ1.40; Δ1.25; Δ0.80; Δ0.70; Δ0.60; Δ0.30) and utilizing the vector pBI101.3 alone as a control, as provided in Table 1. GUS activity was measured in pmolMU/μg protein/min, and the relative activity shown is root activity/ leaf activity.
Figure 6A:
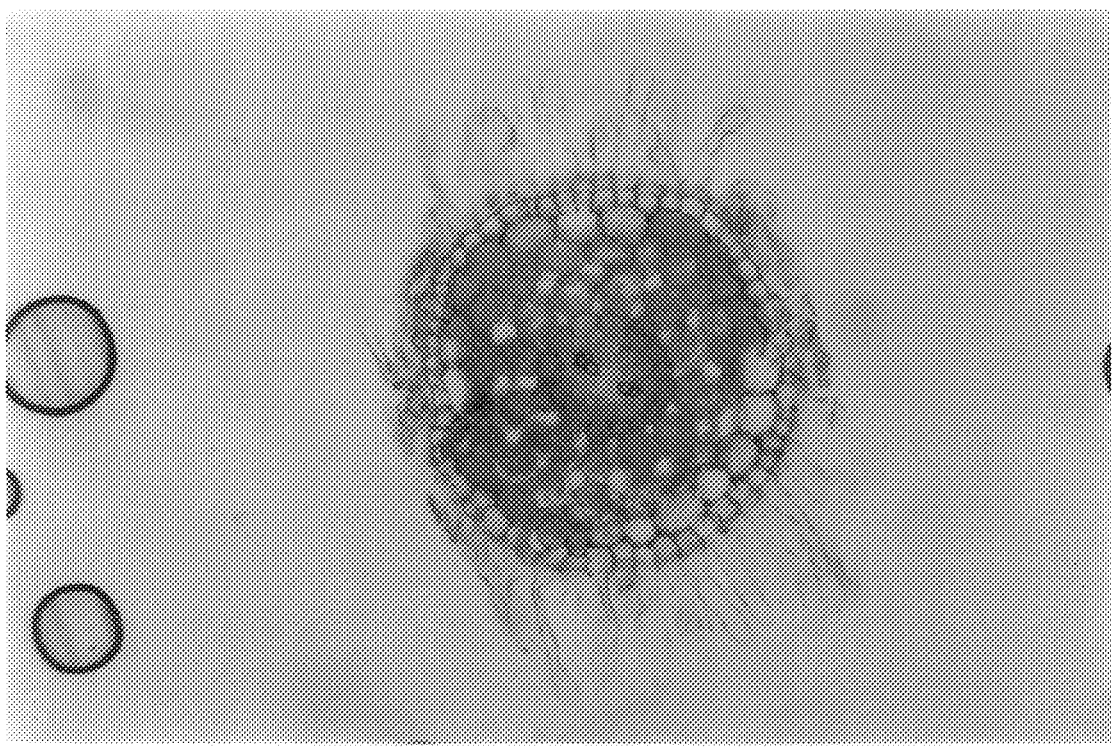
FIG. 6A is a photomicrograph showing the histochemical localization of GUS activity in a transverse section of root from a tobacco plant transformed with a reporter gene (GUS) driven by the Δ2.0 promoter.
Figure 6B:
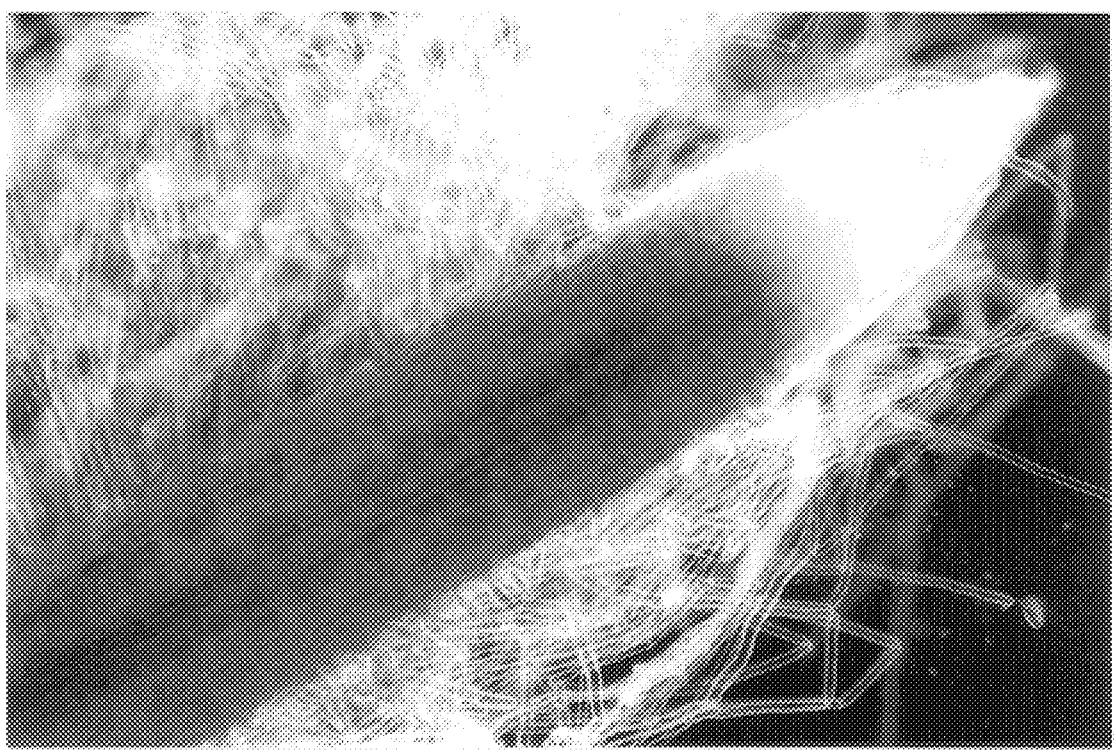
FIG. 6B is a photomicrograph showing the histochemical localization of GUS activity in a root tip from a tobacco plant transformed with a reporter gene (GUS) driven by the Δ2.0 promoter.

FIGS. 5A and 5B further illustrate the organ specific nature of reporter gene expression using TobRD2 promoters. In all instances tested, GUS activity was strictly expressed in the roots and negligible activity, if any, was detected in the stems or leaves of the same transformed tobacco plants. While the level of GUS activity measured in roots transformed with the Δ0.60 and Δ0.30 promoters was equivalent to or less than that provided by the CaMV35S promoter (FIG. 4), FIGS. 5A and 5B illustrate that expression directed by the Δ0.60 and Δ0.30 promoters was root-specific, with negligible activity in stems and leaves, unlike expression directed by the CaMV35S promoter.

The foregoing examples are illustrative of the present invention, and are not to be construed as limiting thereof. The invention is defined by the following claims, with equivalents of the claims to be included therein.

That which is claimed is:

1. An isolated DNA molecule which directs root cortex specific transcription of a downstream heterologous DNA segment in a plant cell, said isolated DNA molecule having a sequence selected from the group consisting of:
  (a) SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9 , and
  (b) DNA sequences which hybridize to isolated DNA having a sequence of (a) above, under conditions represented by a wash stringency of 0.3M NaCl, 0.03M sodium citrate, 0.1% SDS at 60°, and which direct root cortex specific transcription of a downstream heterologous DNA segment in a plant cell.

2. A DNA construct comprising an expression cassette, which construct comprises, in the 5' to 3' direction, a Tobacco RD2 promoter and a heterologous DNA segment positioned downstream from said promoter and operatively associated therewith, said promoter directing the root cortex specific expression of said heterologous DNA segment.

3. A DNA construct comprising an expression cassette, which construct comprises in the 5' to 3' direction, a root cortex specific promoter and a heterologous DNA segment positioned downstream from said promoter and operatively associated therewith, wherein said root cortex specific promoter has a sequence selected from the group consisting of:
  (a) SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9 , and
  (b) DNA sequences which hybridize to isolated DNA having a sequence of (a) above, under conditions represented by a wash stringency of 0.3M NaCl, 0.03M sodium citrate, 0.1% SDS at 60°, and which direct root cortex specific transcription of a downstream heterologous DNA segment in a plant cell.

4. A DNA construct according to claim 3, wherein said construct further comprises a plasmid.

5. A DNA construct according to claim 3, wherein said heterologous DNA segment is a gene coding for an insecticidal protein.

6. A DNA construct according to claim 4, wherein said heterologous DNA segment is a gene coding for a *Bacillus thuringiensis* crystal protein toxic to insects.

7. A plant cell stably transformed with a DNA construct according to claim 3.

8. A method of making a transformed plant, comprising regenerating a plant from a plant cell according to claim 7.

9. An *Agrobacterium tumefaciens* cell containing a DNA construct according to claim 3, and wherein said DNA construct further comprises a Ti plasmid.

10. A method of making a transformed plant, comprising infecting a plant cell with an *Agrobacterium tumefaciens* according to claim 9 to produce a transformed plant cell, and then regenerating a plant from said transformed plant cell.

11. A microparticle carrying a DNA construct according to claim 3, wherein said microparticle is suitable for the ballistic transformation of a plant cell.

12. A method of making a transformed plant, comprising propelling a microparticle according to claim 11 into a plant cell to produce a transformed plant cell, and then regenerating a plant from said transformed plant cell.

13. A plant cell protoplast comprising a DNA construct according to claim 3.

14. A method of making a transformed plant, comprising regenerating a plant from a plant cell protoplast according to claim 13.

15. A transformed plant comprising transformed plant cells, said transformed plant cells containing a heterologous DNA construct, which construct comprises in the 5' to 3' direction, a Tobacco RD2 root cortex specific promoter and a heterologous DNA segment positioned downstream from said promoter and operatively associated therewith, said promoter directing root cortex specific transcription of said heterologous DNA segment.

16. A transformed plant according to claim 15, wherein said promoter has a sequence selected from the group consisting of:
    (a) SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9 , and
    (b) DNA sequences which hybridize to isolated DNA having a sequence of (a) above, under conditions represented by a wash stringency of 0.3M NaCl, 0.03M sodium citrate, 0.1% SDS at 60°, and which direct root cortex specific transcription of a downstream heterologous DNA segment in a plant cell.

17. A transformed plant according to claim 15, wherein said plant is a dicot.

18. A transformed plant according to claim 15, wherein said plant is a monocot.

19. A transformed plant according to claim 15, wherein said plant is a tobacco (*Nicotiana tabacum*) plant.

20. An isolated DNA molecule consisting essentially of a promoter which directs root cortex specific transcription of a downstream heterologous DNA segment in a plant cell and having a sequence selected from the group consisting of SEQ ID NOS:1–9.

21. A DNA construct comprising an expression cassette, which construct comprises, in the 5' to 3' direction, a promoter according to claim 20 and a heterologous DNA segment positioned downstream from said promoter and operatively associated therewith.

22. A transformed plant comprising transformed plant cells, said transformed plant cells containing a DNA construct according to claim 21.

* * * * *